United States Patent
Satchi-Fainaro et al.

(10) Patent No.: US 9,427,474 B2
(45) Date of Patent: *Aug. 30, 2016

(54) CONJUGATES OF A POLYMER, A BISPHOSPHONATE AND AN ANTI-ANGIOGENESIS AGENT AND USES THEREOF IN THE TREATMENT AND MONITORING OF BONE RELATED DISEASES

(71) Applicant: Ramot at Tel-Aviv University Ltd., Tel-Aviv (IL)

(72) Inventors: Ronit Satchi-Fainaro, Tel-Aviv (IL); Keren Miller, Moshav Beit-Elazari (IL); Doron Shabat, Tel-Aviv (IL); Rotem Erez, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/816,228

(22) Filed: Aug. 3, 2015

(65) Prior Publication Data

US 2015/0328330 A1   Nov. 19, 2015

Related U.S. Application Data

(60) Division of application No. 14/158,881, filed on Jan. 20, 2014, now Pat. No. 9,095,618, which is a continuation of application No. 12/993,856, filed as application No. PCT/IL2009/000507 on May 21, 2009, now Pat. No. 8,658,149.

(60) Provisional application No. 61/193,138, filed on Oct. 30, 2008, provisional application No. 61/071,889, filed on May 22, 2008.

(51) Int. Cl.
| | |
|---|---|
| *A61K 31/74* | (2006.01) |
| *A61K 47/48* | (2006.01) |
| *A61K 49/00* | (2006.01) |
| *C07F 9/38* | (2006.01) |
| *C07F 9/655* | (2006.01) |
| *C07F 9/6558* | (2006.01) |
| *C07K 5/065* | (2006.01) |
| *C07K 5/103* | (2006.01) |
| *A61K 31/337* | (2006.01) |
| *A61K 9/16* | (2006.01) |

(52) U.S. Cl.
CPC ....... *A61K 47/48084* (2013.01); *A61K 31/337* (2013.01); *A61K 47/48176* (2013.01); *A61K 47/48338* (2013.01); *A61K 49/0017* (2013.01); *A61K 49/0054* (2013.01); *C07F 9/3873* (2013.01); *C07F 9/65517* (2013.01); *C07F 9/65586* (2013.01); *C07K 5/06078* (2013.01); *C07K 5/1008* (2013.01); *A61K 9/1676* (2013.01); *A61K 2800/57* (2013.01)

(58) Field of Classification Search
CPC ................................................ A61K 47/48084
See application file for complete search history.

(56) References Cited

U.S. PATENT DOCUMENTS

| | | | |
|---|---|---|---|
| 6,884,817 B2 | 4/2005 | Li et al. | |
| 6,949,537 B2 | 9/2005 | Garlich et al. | |
| 7,803,903 B2 | 9/2010 | Kratz | |
| 8,586,019 B2 | 11/2013 | Satchi-Fainaro et al. | |
| 8,658,149 B2 | 2/2014 | Satchi-Fainaro et al. | |
| 2002/0197261 A1 | 12/2002 | Li et al. | |
| 2005/0257114 A1 | 11/2005 | Gorshe | |
| 2005/0287114 A1 | 12/2005 | Wang et al. | |
| 2007/0104719 A1 | 5/2007 | Carter et al. | |
| 2008/0112919 A1 | 5/2008 | Satchi-Fainaro et al. | |
| 2008/0279778 A1 | 11/2008 | Van et al. | |
| 2009/0010887 A1 | 1/2009 | Ben-Sasson | |
| 2010/0022615 A1 | 1/2010 | Fegley et al. | |
| 2011/0135618 A1 | 6/2011 | Koch et al. | |
| 2011/0286923 A1 | 11/2011 | Satchi-Fainaro et al. | |
| 2014/0079638 A1 | 3/2014 | Satchi-Fainaro et al. | |
| 2014/0134111 A1 | 5/2014 | Satchi-Fainaro et al. | |
| 2015/0017115 A1 | 1/2015 | Satchi-Fainaro et al. | |

FOREIGN PATENT DOCUMENTS

| | | |
|---|---|---|
| CN | 101707869 | 5/2010 |
| CN | 102131509 | 7/2011 |
| WO | WO 03/086178 | 10/2003 |
| WO | WO 03/086382 | 10/2003 |
| WO | WO 2004/062588 | 7/2004 |
| WO | WO 2006/012355 | 2/2006 |
| WO | WO 2006/084054 | 8/2006 |
| WO | WO 2007/090094 | 8/2007 |
| WO | WO 2008/034124 | 3/2008 |
| WO | WO 2008/094834 | 8/2008 |
| WO | WO 2008/124735 | 10/2008 |

(Continued)

OTHER PUBLICATIONS

Communication Pursuant to Rule 164(1) EPC and the Supplementary Partial European Search Report Dated Nov. 17, 2014 From the European Patent Office Re. Application No. 09750275.1.
International Preliminary Report on Patentability Dated Dec. 2, 2010 From the International Bureau of WIPO Re. Application No. PCT/IL2009/000507.
International Preliminary Report on Patentability Dated Dec. 2, 2010 From the International Bureau of WIPO Re. Application No. PCT/IL2009/000510.
International Preliminary Report on Patentability Dated Dec. 2, 2010 From the International Bureau of WIPO Re. Application No. PCT/IL2009/000511.
International Preliminary Report on Patentability Dated Sep. 18, 2014 From the International Bureau of WIPO Re. Application No. PCT/IL2013/050195.

(Continued)

*Primary Examiner* — Paul Dickinson

(57) ABSTRACT

Conjugates of polymers or copolymers having attached thereto an anti-angiogenesis agent and a bisphosphonate bone targeting agent, and processes of preparing same, are disclosed.
Pharmaceutical compositions containing these conjugates and uses thereof in the treatment of bone related disorders are also disclosed.

19 Claims, 15 Drawing Sheets

(56) References Cited

FOREIGN PATENT DOCUMENTS

| WO | WO 2008/141110 | 11/2008 |
|---|---|---|
| WO | WO 2009/141823 | 11/2009 |
| WO | WO 2009/141826 | 11/2009 |
| WO | WO 2009/141827 | 11/2009 |
| WO | WO 2013/132485 | 9/2013 |

OTHER PUBLICATIONS

Figure 1:
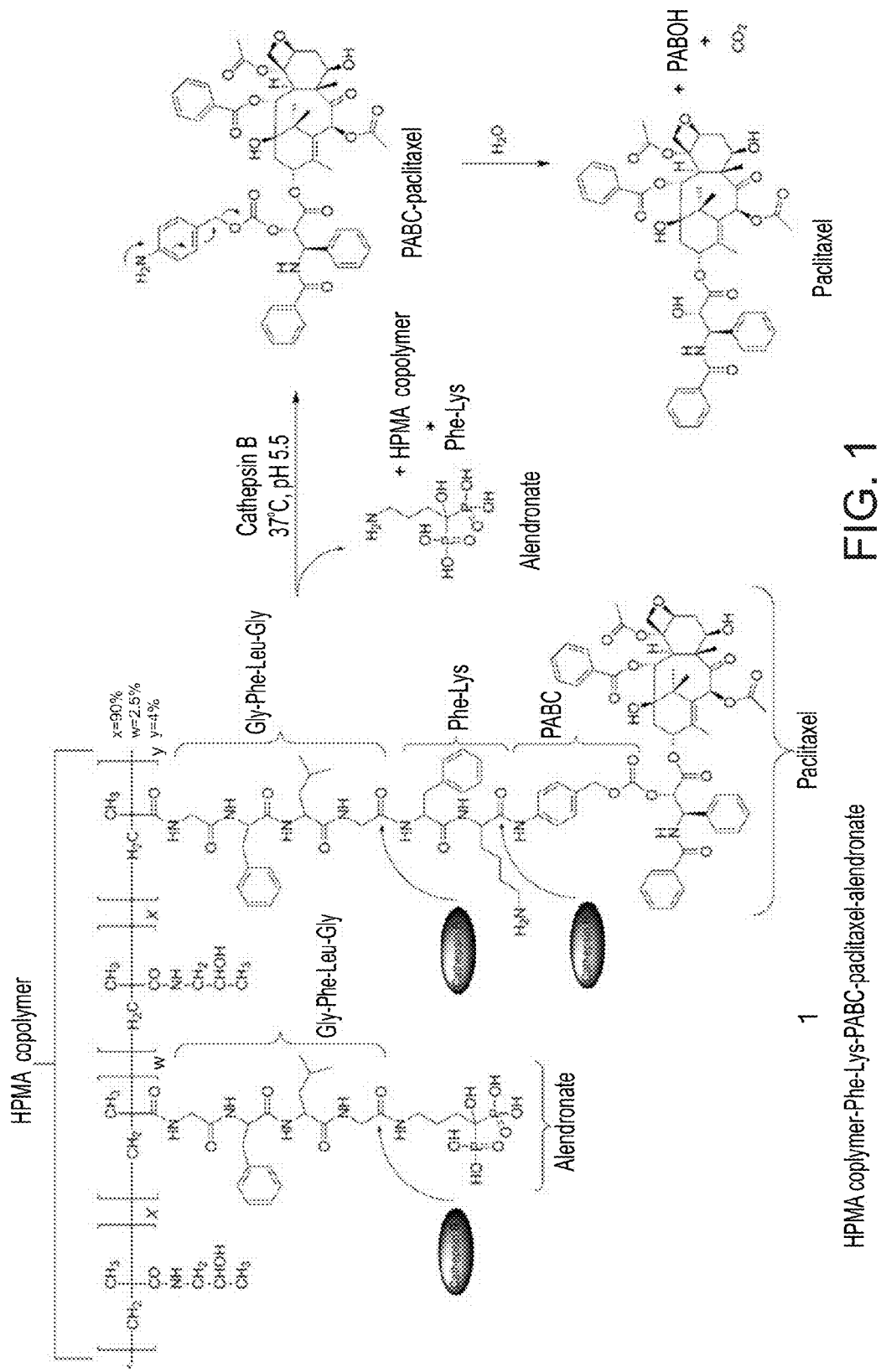

International Search Report and the Written Opinion Dated Dec. 2, 2009 From the International Searching Authority Re. Application No. PCT/IL09/00510.
International Search Report and the Written Opinion Dated Nov. 5, 2009 From the International Searching Authority Re. Application No. PCT/IL09/00511.
International Search Report and the Written Opinion Dated Jun. 16, 2013 From the International Searching Authority Re. Application No. PCT/IL2013/050195.
International Search Report and the Written Opinion Dated Nov. 25, 2009 From the International Searching Authority Re. Application No. PCT/IL09/00507.
Notice of Allowance Dated Jun. 21, 2013 From the US Patent and Trademark Office Re. U.S. Appl. No. 12/993,853.
Notice of Reexamination Dated Feb. 16, 2015 From the Patent Reexamination Board of State Intellectual Property Office of the People's Republic of China Re. Application No. 200980128587.1 and Its Translation Into English.
Notice of Reexamination Dated Jul. 29, 2014 From the Patent Reexamination Board of State intellectual Property Office of the People's Republic of China Re. Application No. 200980128587.1 and Its Translation Into English.
Official Action Dated May 1, 2014 From the US Patent and Trademark Office Re. U.S. Appl. No. 14/158,881.
Official Action Dated Mar. 4, 2013 From the US Patent and Trademark Office Re. U.S. Appl. No. 12/993,856.
Official Action Dated Apr. 7, 2014 From the US Patent and Trademark Office Re. U.S. Appl. No. 14/082,224.
Official Action Dated Nov. 13, 2014 From the US Patent and Trademark Office Re. U.S. Appl. No. 14/082,224.
Official Action Dated Dec. 15, 2014 From the US Patent and Trademark Office Re. U.S. Appl. No. 14/158,881.
Official Action Dated Apr. 18, 2013 From the US Patent and Trademark Office Re. U.S. Appl. No. 12/993,855.
Official Action Dated May 21, 2015 From the US Patent and Trademark Office Re. U.S. Appl. No. 14/082,224.
Official Action Dated Jan. 31, 2013 From the US Patent and Trademark Office Re. U.S. Appl. No. 12/993,853.
Restriction Official Action Dated Dec. 3, 2012 From the US Patent and Trademark Office Re. U.S. Appl. No. 12/993,853.
Restriction Official Action Dated Oct. 11, 2012 From the US Patent and Trademark Office Re. U.S. Appl. No. 12/993,856.
Restriction Official Action Dated Jun. 23, 2014 From the US Patent and Trademark Office Re. U.S. Appl. No. 14/242,901.
Supplementary European Search Report and the European Search Opinion Dated Sep. 10, 2014 From the European Patent Office Re. Application No. 09750179.3.
Supplementary European Search Report and the European Search Opinion Dated Mar. 19, 2015 From the European Patent Office Re. Application No. 09750275.1.
Supplementary European Search Report and the European Search Opinion Dated Jul. 21, 2014 From the European Patent Office Re. Application No. 09750278.5.
Translation of Decision on Rejection Dated Mar. 12, 2013 From the State Intellectual Property Office of the People's Republic of China Re. Application No. 200980128587.1.
Translation of Office Action Dated Aug. 1, 2012 From the State Intellectual Property Office of the People's Republic of China Re. Application No. 200980128587.1.
Translation of Office Action Dated Jan. 5, 2012 From the State Intellectual Property Office of the People's Republic of China Re. Application No. 200980128588.6.
Translation of Office Action Dated Sep. 26, 2011 From the State Intellectual Property Office of the People's Republic of China Re. Application No. 200980128587.1.
Alavi et al. "Chemoresistance of Endothelial Cells Induced by Basic Fibroblast Growth Factor Depends on Raf-1-Mediated Inhibition of the Proapoptotic Kinase, ASK1", Cancer Research, XP055136030, 67(6): 2766-2772, Mar. 15, 2007. Abstract, Fig.2C.
Baabur-Cohen et al. "Recent Progress in Polymer Therapeutics as Nanomedicines", Handbook of Harnessing Biomaterials in Nanomedicine: Preparation, Toxicity, and Applications, Chap.4: 77-122, 2012.
Chen et al. "Synthesis and Biological Evaluation of Dimeric RGD Peptide-Paclitaxel Conjugate as a Model for Integrin-Targeted Drug Delivery", Journal of Medicinal Chemistry, 48: 1098-1106, 2005. P.1098, r-h Col., Para Full 1 of the Col., Fig.1.
Duncan "Polymer Conjugates as Anticancer Nanomedicines", Nature Reviews Cancer, 6: 688-701, Sep. 2006.
Eldar-Boock et al. "Integrin-Assisted Drug Delivery of Nano-Scaled Polymer Therapeutics Bearing Paclitaxel", Biomaterials, XP028369082, 32(15): 3862-3874, May 2011.
Greco et al. "Combination Therapy: Opportunities and Challenges for Polymer-Drug Conjugates as Anticancer Nanomedicines", Advanced Drug Delivery Reviews, 61: 1203-1213, 2009.
Iiruby et al. "Iiydroxybisphosphonate-Containing Polymeric Drug-Delivery Systems Designed for Targeting Into Bone Tissue", Journal of Applied Polymer Science, XP008076287, 101(5): 3192-3201, Jan. 1, 2006. Abstract, p. 3193, col. 2, Last Line, p. 3200, col. 2, First Line.
Lee et al. "Anthracycline Chemotherapy Inhibits HIF-1 Transcriptional Activity and Tumor-Induced Mobilization of Circulating Angiogenic Cells", Proc. Natl. Acad. Sci, USA, PNAS, XP055135983, 106(7): 2353-2358, Feb. 17, 2009. Abstract.
Marsili et al. "Interaction of DDSDEEN Peptide With N-CAM Protein. Possible Mechanism Enhancing Neuronal Differentiation", Peptides, 29: 2232-2242, 2008.
Meerum Terwogt et al. "Phase I Clinical and Pharmacokinetic Study of PNU166945, A Novel Water-Soluble Polymer-Conjugated Prodrug of Paclitaxel", Anti-Cancer Drug, XP008124180, 12(4): 315-323, Apr. 1, 2001. Fig.1.
Miller et al. "A Novel Bi-Specific Targeting Agent Based on a Polymer-Alendronate-Taxane Conjugate to Target Metastatic Prostate Carcinomas", Proceedings of the American Association for Cancer Research Annual Meeting, XP009179745, 49: 84-85, # 369, Apr. 2008. & 99th Annual Meeting of the American Association for Cancer Research, AACR, San Diego, CA, USA, Apr. 12-16, 2008. Title, Abstract.
Miller et al. "Targeting Bone Metastases With a Bispecific Anticancer and Antiangiogenic Polymer-Alensronate-Taxane Conjugate", Angewandte Chemie International Edition, XP002680271, 48(16): 2949-2954, Apr. 6, 2009. 'HPMA-Alendronate-TNP470 Conjugate, for Treating Bone Cancer', Title, p. 2949, First Line of col. 2, p. 2949, Last 5 Lines, p. 2950, First Line.
Mitra et al. "Comparison of Polymeric Conjugates of Mono- and Bi-Cyclic RGD Peptide for Targeting Tumor Angiogenesis", 2006 National Biotechnology Conference, The AAPS Journal, 8(S1): # 127, 2006. § 1, 3-4.
Mitra et al. "Polymeric Conjugates of Mono- and Bi-Cyclic AlphaVBeta3 Binding Peptides for Tumor Targeting", Journal of Controlled Release, 114: 175-183, 2006.
Mitra et al. "Polymer-Peptide Conjugates for Angiogenesis Targeted Tumor Radiotherapy", Nuclear Medicine and Biology, 33: 43-52, 2006.
O'Hare et al. "Polymeric Drug-Carriers Containing Doxorubicin and Melanocyte-Stimulating Iiormone: In Vitro and In Vivo Evaluation Against Murine Melanoma", Journal of Drug Targeting, 1: 217-229, 1993.

(56) References Cited

OTHER PUBLICATIONS

Pan et al. "Backbone Degradable Multiblock N-(2-Hydroxypropyl)Methacrylamide Copolymer Conjugates Via Reversible Addition Fragmentation Chain Transfer Polymerization and Thiol-Ene Coupling Reaction", Biomacromolecules, 12(1): 247-252, Jan. 10, 2011.
Pan et al. "Water-Soluble HPMA Copolymer—Prostaglandin E1, Conjugates Conatining a Cathepsin K Sensitive Spacer", Journal of Drug Targeting, XP008140389, 14(6): 425-435, 2006. Abstract.
Rihova et al. "Clinical Implications of N-(2-Hydroxypropyl)Methacrylamide Copolymers", Current Pharmaceutical Biotechnology, XP008124188, 4(5): 311-322, Oct. 1, 2003. p. 313, col. 1, Penultimate, p. 314, col. 1 Last Line, p. 316, Fig.4.
Satchi-Fainaro et al. "Synthesis and Characterization of a Catalytic Antibody-HPMA Copolymer-Conjugate as a Tool for Tumor Selective Prodrug Activation", Bioorganic & Medicinal Chemistry, 10(9): 3023-3029, 2002.
Satchi-Fainaro et al. "Targeting Angiogenesis With a Conjugate of HPMA Copolymer and TNP-470", Nature Medicine, XP002542562, 10(3): 255-261, Mar. 2004. 'HPMA—TNP470 Conjugates', Abstract.
Segal et al. "Design and Development of Polymer Conjugates as Anti-Angiogenic Agents", Advanced Drug Delivery Reviews, XP026698380, 61(13): 1159-1176, Nov. 12, 2009. Sections 3, 4, p. 1164-1168.
Segal et al. "Enhanced Anti-Tumor Activity and Safety Profile of Targeted Nano-Scaled HPMA Copolymer-Alendronate-TNP-470 Conjugate in the Treatment of Bone Malignances", Biomaterials, 32(19): 4450-4463, Jul. 2011.
Segal et al. "Targeting Angiogenesis-Dependent Calcified Neoplasms Using Combines Polymer Therapeutics", PLoS ONE, XP002727812, 4(4): e5233-1-e5233-16, Apr. 21, 2009. Abstract, p. e5233, col. 2, First Full Para, Supporting Info.
Seymour et al. "Hepatic Drug Targeting: Phase I Evaluation of Polymer-Bound Doxorubicin", Journal of Clinical Oncology, 20(6): 1668-1676, Mar. 15, 2002.
Uludag "Bisphosphonates as A Foundation of Drug Delivery to Bone", Current Pharmaceutical Design, 8: 1929-1944, 2002.
Van Hagen et al. "Evaluation of a Radiolabelled Cyclic DTPA-RGD Analogue for Tumour Imaging and Radionuclide Therapy", International Journal of Cancer, 90(4): 186-198, Aug. 2000.
Wan et al. "Targeting Endothelial Cell Using HPMA Copolymer-Doxorubicin-RGD Conjugates", Proceedings of the 30th Annual Meeting of the International Symposium on Controlled Release Bioactive Materials, XP009178957, 30: 491492, #491, Jan. 1, 2003.
Wang et al. "Paclitaxel at Ultra Low Concentrations Inhibits Angiogenesis Without Affecting Cellular Microtube Assembly", Anti-Cancer Drugs, 14: 13-19, 2003.
Wang et al. "Synthesis and Evaluation of Water-Soluble Polymeric Bont-Targeted Drug Delivery Systems", Bioconjugate Chemistry, XP002290582, 14: 853-859, Jan. 2003. 'Polymer—Fluorescein—Alendronate Conjugate', Abstract, Last Line of Conclusion.
Office Action Dated Dec. 21, 2015 From the Patent Office of the State Intellectual Property Office of the People's Republic of China Re. Application No. 201380018242.7 and Its Translation Into English.
Communication Pursuant to Rule 164(1) EPC [Partial Supplementary European Search Report] Dated Oct. 14, 2015 From the European Patent Office Re. Application No. 13758298.7.
Duncan et al. "Polymer-Drug Conjugates, PDEPT and PELT: Basic Principles for Design and Transfer From the Laboratory to Clinic", Journal of Controlled Release, XP027296078, 74(1-3): 135-146, Jul. 6, 2001.
Jensen et al. "Targeting the Neural Cell Adhesion Molecule in Cancer", Cancer Letters, XP022310543, 258(1): 9-21, Oct. 18, 2007.
Zhang "Poly (L-Glutamic Acid)-Paclitaxel Conjugates for Cancer Treatment", Biomedical Science, Engineering and Technology, XP055216033, Chap.24: 587-603, Jan. 20, 2012. Compounds PG-PTX.
Hearing Notice Dated Jun. 17, 2016 From the Government of India, Patent Office, Intellectual Property Building Re. Application No. 2558/MUMNP/2010.

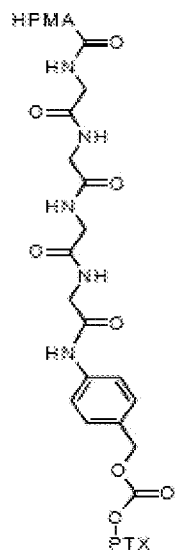
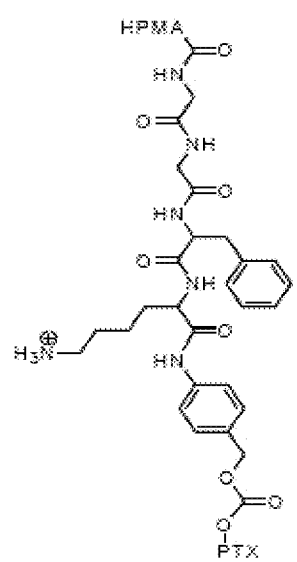
FIG.6A　　　　　　　　　　FIG. 6B
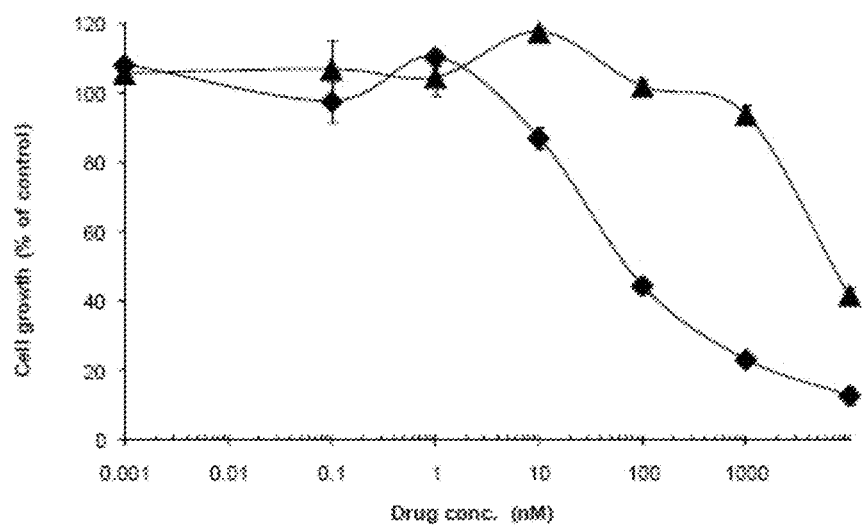
FIG.6C

SEQUENCE LISTING

```
<160> NUMBER OF SEQ ID NOS: 27

<210> SEQ ID NO 1
<211> LENGTH: 3
<212> TYPE: PRT
<213> ORGANISM: Artificial sequence
<220> FEATURE:
<223> OTHER INFORMATION: Synthetic peptide

<400> SEQUENCE: 1

Arg Gly Asp
1

<210> SEQ ID NO 2
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA conjugate
<220> FEATURE:
<221> NAME/KEY: misc_feature
<222> LOCATION: (1)..(8)
<223> OTHER INFORMATION: Enantiomer D
<220> FEATURE:
<221> NAME/KEY: misc_feature
<222> LOCATION: (8)..(8)
<223> OTHER INFORMATION: Alendronate Conjugate

<400> SEQUENCE: 2

Asp Asp Asp Asp Asp Asp Asp Asp
1               5

<210> SEQ ID NO 3
<211> LENGTH: 4
<212> TYPE: PRT
<213> ORGANISM: Artificial sequence
<220> FEATURE:
<223> OTHER INFORMATION: Synthetic peptide

<400> SEQUENCE: 3

Gly Phe Leu Gly
1
```

```
<210> SEQ ID NO 4
<211> LENGTH: 3
<212> TYPE: PRT
<213> ORGANISM: Artificial sequence
<220> FEATURE:
<223> OTHER INFORMATION: Synthetic peptide

<400> SEQUENCE: 4

Ala Leu Ala
1

<210> SEQ ID NO 5
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Cit

<400> SEQUENCE: 5

Xaa Val
1

<210> SEQ ID NO 6
<211> LENGTH: 3
<212> TYPE: PRT
<213> ORGANISM: Artificial sequence
<220> FEATURE:
<223> OTHER INFORMATION: Synthetic peptide

<400> SEQUENCE: 6

Gly Leu Gly
1

<210> SEQ ID NO 7
<211> LENGTH: 3
<212> TYPE: PRT
<213> ORGANISM: Artificial sequence
<220> FEATURE:
<223> OTHER INFORMATION: Synthetic peptide

<400> SEQUENCE: 7

Gly Phe Gly
1

<210> SEQ ID NO 8
<211> LENGTH: 4
<212> TYPE: PRT
<213> ORGANISM: Artificial sequence
<220> FEATURE:
<223> OTHER INFORMATION: Synthetic peptide

<400> SEQUENCE: 8

Gly Leu Phe Gly
1

<210> SEQ ID NO 9
<211> LENGTH: 4
<212> TYPE: PRT
<213> ORGANISM: Artificial sequence
<220> FEATURE:
<223> OTHER INFORMATION: Synthetic peptide

<400> SEQUENCE: 9
```

```
Ala Leu Ala Leu
1

<210> SEQ ID NO 10
<211> LENGTH: 2
<212> TYPE: PRT
<213> ORGANISM: Artificial sequence
<220> FEATURE:
<223> OTHER INFORMATION: Synthetic peptide

<400> SEQUENCE: 10

Phe Lys
1

<210> SEQ ID NO 11
<211> LENGTH: 6
<212> TYPE: PRT
<213> ORGANISM: Artificial sequence
<220> FEATURE:
<223> OTHER INFORMATION: Synthetic peptide

<400> SEQUENCE: 11

Gly Phe Leu Gly Phe Lys
1               5

<210> SEQ ID NO 12
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA-Paclitaxel conjugate
<220> FEATURE:
<221> NAME/KEY: misc_feature
<222> LOCATION: (2)..(2)
<223> OTHER INFORMATION: Alendronate conjugate

<400> SEQUENCE: 12

Phe Lys
1

<210> SEQ ID NO 13
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Paclitaxel conjugate

<400> SEQUENCE: 13

Phe Lys
1

<210> SEQ ID NO 14
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA conjugate
<220> FEATURE:
```

```
<221> NAME/KEY: misc_feature
<222> LOCATION: (4)..(4)
<223> OTHER INFORMATION: Paclitaxel conjugate

<400> SEQUENCE: 14

Gly Gly Gly Gly
1

<210> SEQ ID NO 15
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA conjugate
<220> FEATURE:
<221> NAME/KEY: misc_feature
<222> LOCATION: (4)..(4)
<223> OTHER INFORMATION: Paclitaxel conjugate

<400> SEQUENCE: 15

Gly Gly Phe Lys
1

<210> SEQ ID NO 16
<211> LENGTH: 2
<212> TYPE: PRT
<213> ORGANISM: Artificial sequence
<220> FEATURE:
<223> OTHER INFORMATION: Synthetic peptide

<400> SEQUENCE: 16

Arg Arg
1

<210> SEQ ID NO 17
<211> LENGTH: 4
<212> TYPE: PRT
<213> ORGANISM: Artificial sequence
<220> FEATURE:
<223> OTHER INFORMATION: Synthetic peptide

<400> SEQUENCE: 17

Gly Phe Ala Leu
1

<210> SEQ ID NO 18
<211> LENGTH: 4
<212> TYPE: PRT
<213> ORGANISM: Artificial sequence
<220> FEATURE:
<223> OTHER INFORMATION: Synthetic peptide

<400> SEQUENCE: 18

Gly Gly Gly Gly
1

<210> SEQ ID NO 19
<211> LENGTH: 4
<212> TYPE: PRT
<213> ORGANISM: Artificial sequence
<220> FEATURE:
<223> OTHER INFORMATION: Synthetic peptide

<400> SEQUENCE: 19
```

Gly Gly Phe Lys
1

<210> SEQ ID NO 20
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: Norleucine (Nle)

<400> SEQUENCE: 20

Gly Gly Pro Xaa
1

<210> SEQ ID NO 21
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA conjugate
<220> FEATURE:
<221> NAME/KEY: MOD_RES
<222> LOCATION: (4)..(4)
<223> OTHER INFORMATION: p-nitrophenol (ONp) activated amino acid

<400> SEQUENCE: 21

Gly Phe Leu Gly
1

<210> SEQ ID NO 22
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA conjugate
<220> FEATURE:
<221> NAME/KEY: MOD_RES
<222> LOCATION: (2)..(2)
<223> OTHER INFORMATION: p-nitrophenol (ONp) activated amino acid

<400> SEQUENCE: 22

Gly Gly
1

<210> SEQ ID NO 23
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: methacryloyl conjugate
<220> FEATURE:
<221> NAME/KEY: MOD_RES
<222> LOCATION: (2)..(2)
<223> OTHER INFORMATION: p-nitrophenol (ONp) activated amino acid

<400> SEQUENCE: 23

```
Gly Gly
1

<210> SEQ ID NO 24
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: methacryloyl conjugate
<220> FEATURE:
<221> NAME/KEY: MOD_RES
<222> LOCATION: (4)..(4)
<223> OTHER INFORMATION: p-nitrophenol (ONp) activated amino acid

<400> SEQUENCE: 24

Gly Phe Leu Gly
1

<210> SEQ ID NO 25
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: HPMA conjugate

<400> SEQUENCE: 25

Gly Phe Leu Gly
1

<210> SEQ ID NO 26
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: p-nitrophenol (ONp) activated amino acid

<400> SEQUENCE: 26

Gly Leu Phe Gly
1

<210> SEQ ID NO 27
<211> LENGTH: 2
<212> TYPE: PRT
<213> ORGANISM: Artificial sequence
<220> FEATURE:
<223> OTHER INFORMATION: Synthetic peptide

<400> SEQUENCE: 27

Gly Gly
1
```

CONJUGATES OF A POLYMER, A BISPHOSPHONATE AND AN ANTI-ANGIOGENESIS AGENT AND USES THEREOF IN THE TREATMENT AND MONITORING OF BONE RELATED DISEASES

RELATED APPLICATIONS

This application is a division of U.S. patent application Ser. No. 14/158,881 filed on Jan. 20, 2014, which is a continuation of U.S. patent application Ser. No. 12/993,856 filed on Nov. 22, 2010, now U.S. Pat. No. 8,658,149, which is a National Phase of PCT Patent Application No. PCT/IL2009/000507 having International filing date of May 21, 2009, which claims the benefit of priority of U.S. Provisional Patent Application Nos. 61/193,138 filed on Oct. 30, 2008 and 61/071,889 filed on May 22, 2008. The contents of the above applications are all incorporated by reference as if fully set forth herein in their entirety.

SEQUENCE LISTING STATEMENT

The ASCII file, entitled 63378SequenceListing.txt, created on Aug. 3, 2015, comprising 8,192 bytes, submitted concurrently with the filing of this application is incorporated herein by reference.

FIELD AND BACKGROUND OF THE INVENTION

The present invention, in some embodiments thereof, relates to chemical conjugates and their use in therapy and diagnosis and, more particularly, but not exclusively, to chemical conjugates of a polymer having attached thereto an anti-angiogenesis agent and a bone targeting moiety, which are useful in the diagnosis, treatment and monitoring of bone related diseases and disorders such as bone cancer and bone metastases.

Osteosarcoma is the most common type of primary bone cancer and classified as a malignant mesenchymal neoplasm in which the tumor directly produces defective osteoid (immature bone). It is a highly vascular and extremely destructive malignancy that most commonly arises in the metaphyseal ends of long bones. Over the past two decades, multimodality treatment consisting of aggressive chemotherapy combined with radical surgical resection, has been the mainstay of osteosarcoma management, with achievable 5 year survival rates of 50 to 70% in patients who do not have metastatic disease at presentation. Several strategies were proposed, such as immune-based therapy, tumor-suppressor or suicide gene therapy, or anticancer drugs that are not commonly used in osteosarcoma. However, still one-third of patients die from this devastating type of cancer, and for those with unresectable disease there are no curative systemic therapies.

Prostate cancer is the most common cancer of males in industrialized countries and the second leading cause of male cancer mortality. Mortality in these patients is not due to primary tumor growth, but rather due to complications caused by metastases to vital organs. Prostate cancer predominantly metastasizes to bone, but other organ sites are affected including the lung, liver, and adrenal gland.

Breast cancer also often metastasizes into bones.

Bone metastases incidence in patients with advanced metastatic disease is approximately 70%. Bone metastases are associated with considerable skeletal morbidity, including severe bone pain, pathologic fracture, spinal cord or nerve root compressions, and hypercalcemia of malignancy. Chemotherapy agents, hormonal deprivation and bisphosphonates are the common treatments for advanced metastatic disease. However, with time, the disease progresses to a phase when the standard therapy fails to control the malignancy and furtherer progresses to a highly chemotherapy-resistant state.

In recent years, it has become clear that tumor progression and metastases formation is adequately dependent on angiogenesis. Angiogenesis is now recognized as an important control point in cancer therapy. As a result, the microvascular endothelial cell, recruited by a tumor, has become an important second target in cancer therapy. Microvascular endothelial cells, unlike the tumor cells themselves, do not tend to develop drug resistance. Tumor endothelial cells are drug sensitive for long periods of time and may be treated with cytotoxic agents in an "antiangiogenic schedule". This schedule involves the administration of chemotherapy in low doses, well below the maximum tolerated dose (MTD), in close intervals for extended periods of time (metronomic dosing). As a result, acute toxicity should be avoided and the drugs may be administered to a longer period, eventually converting cancer to a chronic manageable disease. Although this approach has shown promising results for non-small cell lung cancer, breast and ovarian cancer, even low doses of chemotherapeutic drugs, when given metronomically for long periods of time accumulate in the body and cause damage (Browder et al., Antiangiogenic scheduling of chemotherapy improves efficacy against experimental drug-resistant cancer, *Cancer Res* 2000; 60: 1878-1886).

The taxane paclitaxel (PTX) is a potent anti-neoplastic agent. Paclitaxel is a clinically well established and highly effective anti-neoplastic medication as monotherapy and in combination therapy used for the treatment of metastatic prostate and breast cancer. The primary mode of action of paclitaxel is to promote microtubulin assembly and stabilize them, preventing their depolymerization and thereby inhibiting microtubule dynamics which causes impaired mitosis, leading to cell cycle arrest and finally to apoptosis. Despite its strong anticancer activity, paclitaxel is poorly water-soluble and exhibits serious dose-limiting toxicities and hypersensitivity reactions which originate from the formulating vehicle cremophor EL and the absence of selectivity for target tissue (Gelderblom et al., 2001, *Eur J Cancer* 37 (13), 1950-8; Bhalla, K. N. *Oncogene* 2003; 22:9075-90861. In recent years, it has become evident that paclitaxel at low doses has antiangiogenic properties (Wang, et al. *Anticancer Drugs* 2003; 14: 13-19).

The antiangiogenic schedule of low doses of paclitaxel administered metronomically have been tested on breast cancer patients, and showed promising results with reduced toxicity [Munoz et al., *breast,* 14:466-79 (2005)]. However, even low doses of paclitaxel, given metronomically, caused side effects.

There are currently eight approved anti-cancer therapies with recognized antiangiogenic properties. These agents, which interrupt critical cell signaling pathways involved in tumor angiogenesis and growth, can be divided into two primary categories: (1) monoclonal antibodies directed against specific proangiogenic factors and/or their receptors; (Avastin, Erbitux, Vectibix, Herceptin) and (2) small molecule tyrosine kinase inhibitors (TKIs) of multiple proangiogenic growth factor receptors (Tarveca, Nexavar, Sutent). Inhibitors of mTOR (mammalian target of rapamycin) represent a third, smaller category of antiangiogenic therapies with one currently approved agent (Torisel). In addition, at least two other approved angiogenic agents may indirectly inhibit angiogenesis through mechanisms that are not completely understood (Velcade, Celgene)

The first FDA-approved angiogenesis inhibitor, Bevacizumab (Avastin, Genentech) a monoclonal antibody to vascular endothelial growth factor (VEGF), has recently been approved for metastatic colon cancer treatment in conjunction with standard conventional chemotherapy.

The largest class of drugs that block angiogenesis are the multi-targeted tyrosine kinase inhibitors (TKIs) that target the VEGF receptor (VEGFR). These drugs such as sunitinib (Sutent, Pfizer), Sorafenib (Nexavar, Bayer/Onyx Pharmaceuticals) and Erlotinib (Tarveca, Gennentech/OSI/Roche) have the advantages of hitting multiple targets, convenient oral administration, and cost effectiveness. While these drugs exhibit promising efficacy, their use is limited by their lack of target specificity, which leads to unexpected toxicity [Cabebe et al. *Curr Treat Options Oncol* 2007; 8:15-27].

Water-soluble copolymers such as hydroxypropyl methacrylate (HPMA) are biocompatible, non-immunogenic and non-toxic carriers that enable specific delivery into tumor tissue (Satchi-Fainaro et al. *Nat Med* 2004; 10:255-261). These macromolecules do not diffuse through normal blood vessels but rather accumulate selectively in the tumor site because of the enhanced permeability and retention (EPR) effect. This phenomenon of passive diffusion through the hyperpermeable neovasculature and localization in the tumor interstitium is observed in many solid tumors for macromolecular agents and lipids. Furthermore, conjugation to copolymers, such as HPMA, should restrict the passage through the blood brain bather and would prolong the circulating half-life of the drugs, hence inhibiting the growth of tumor endothelial and epithelial cells by exposing the cells to the conjugated drugs in the circulation for a longer time compared to the free drugs.

An example of the favorable characteristics obtained by conjugation of an anti-angiogenesis agent to HPMA has been described by Satchi-Fainaro et al. in WO 03/086382. This patent application teaches conjugates of water-soluble polymers and the anti-angiogenesis agent TNP-470, and their use as anti-tumor agents, in particular their use as carriers of TNP-470 into tumor vessels, and their effect on the neurotoxicity of TNP-470. According to the teachings of WO 03/086382, an exemplary such conjugate, HPMA-(TNP-470) conjugate (caplostatin), exhibited superior anti-tumor activity together with a reduced level of toxicity, as compared with TNP-470 alone. WO 03/086382 further suggests incorporation of a targeting ligand, such as RGD (SEQ ID NO:1) or antibodies.

The use of HPMA-TNP-470 conjugate for the treatment of angiogenesis related conditions has also been described in WO 03/086178.

Another example of the increased activity yet reduced toxicity obtained by conjugation of anti-tumor drugs to water-soluble polymers is presented in U.S. Pat. No. 6,884,817.

A HPMA copolymer conjugate of paclitaxel has also been described by Meerum Terwogt et al. [PNU166945; *Anticancer drugs* 2001; 12:315-323]. This conjugate was aimed at improving drug solubility and providing controlled release of paclitaxel Bisphosphonates, such as alendronate, are molecules used to treat osteoporosis, bone metastases and to prevent bone fractures. These compounds exhibit an exceptionally high affinity to the bone-mineral hydroxyapatite, and therefore are known to be used also as a targeting moiety (Uludag, H. *Curr Pharm Des* 2002; 8: 1929-1944).

Alendronate is considered potent for the treatment of bone related diseases and cancer-associated hypercalcemia. It was shown to have antitumor effect in several in vivo cancer models through several different mechanisms [Tuomela et al. 2008, *BMC Cancer* 8:81; Molinuevo et al. 2007, *Eur J Pharmacol* 562:28-33; Hashimoto et al. 2005, *Cancer Res* 65: 540-545]. In addition, alendronate was found to have anti-angiogenic activity through (i) suppression of VEGF-induced Rho activation in an ovarian cancer model [Hashimoto et al. 2007, *Biochem Biphys Res Commun* 354: 478-484], (ii) inhibition of farnesyl pyrophosphate synthase, in the mevalonate pathway [Russell R G 2007, *Pediatrics* 119 Suppl 2: S150-162]; and (iii) regulation of cellular level of MMP-2 expression in osteosarcoma cell lines [Cheng et al. 2004, *Pediatr Blood Cancer* 42; 410-415].

WO 2004/062588 teaches water soluble polymeric conjugate for bone targeted drug delivery with improved pharmacokinetics parameters and better water solubility of the loaded drugs. The polymeric drug delivery systems taught by this application are based on hydroxypropyl methacrylate (HPMA) conjugates of bone-targeting drugs such as alendronate and D-Asp$_8$ (SEQ ID NO: 2) together with a bone-related therapeutic agent (e.g., tetracycline).

PK2 (FCE28069) is a HPMA copolymer-doxorubicin-galactosamine conjugate, which was designed as a treatment for hepatocellular carcinoma or secondary liver disease [Seymour et al. *Journal of Clinical Oncology* 2002; 20: 1668-1676]. Doxorubicin is an anthracycline antibiotic with limited solubility in physiological fluids, and is a well established anti-neoplastic drug. Galactosamine binds to the hepatic asialoglycoprotein receptor (ASGPR) thus serving as a specific hepatic targeting moiety. These components are linked to the HPMA polymer via an enzymatically biodegradable linker which permits the release of free doxorubicin within the liver, thus increasing the drug concentration in its site of action. The enzymatic degradable linker is a tetrapeptide spacer (Gly-Phe-Leu-Gly; SEQ ID NO: 3), designed for cleavage by lysosomal cathepsins.

O'hare et al. [*Journal of Drug Targeting* 1993; 1:217-229] have synthesized HPMA copolymers containing doxorubicin and melanocyte stimulating hormone (MSH) as a melanoma specific targeting moiety. Both the doxorubicin and the melanocyte stimulating hormone were linked to the HPMA polymer via an enzymatically biodegradable linker.

Hruby et al. [*Journal of Applied Polymer Science* 2006; 101:3192-3201] have prepared and synthesized novel polymeric drug-delivery systems designed for bone targeting of anti-neoplastics based on biocompatible HPMA copolymers containing hydroxybisphosphonate targeting moieties and the model drugs radiotherapeutics $^{125}$I, imaging agent $^{111}$In, or the anticancer drug Doxorubicin.

SUMMARY OF THE INVENTION

Currently known agents used for treating bone related cancer and other angiogenesis-related conditions, at doses where anti-tumor activity is achieved, are characterized by high toxicity, which limits their use. In a search for modes of modifying currently known anti-angiogenesis agents so as to enable higher therapeutic efficacy thereof together with a reduced level of side effects, the present inventors have designed and successfully prepared and practiced novel conjugates of a hydroxypropyl methacrylamide (HPMA) copolymer, an anti-angiogenesis agent such as paclitaxel, and a bone targeting agent such as alendronate (ALN, a bisphosphonate), in which the anti-angiogenesis agent and the bone targeting agent are conjugated to the HPMA polymer via biodegradable linkers.

According to an aspect of some embodiments of the invention there is provided a conjugate comprising a polymeric backbone having attached thereto an anti-angiogenesis agent and a bisphosphonate bone targeting moiety, the polymeric backbone being derived from a polymer selected from the group consisting of dextran, a water soluble polyamino acid, a polyethylenglycol (PEG), a polyglutamic acid (PGA), a polylactic acid (PLA), a polylactic-co-glycolic (PLGA), a poly(D,L-lactide-co-glycolide) (PLA/PLGA), a poly(hydroxyalkylmethaacrylamide), a polyglycerol, a polyamidoamine (PAMAM), and a polyethylenimine (PEI).

According to some embodiments, the anti-angiogenesis agent being selected from the group consisting of paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, a matrix metalloproteinase, penicillamine, PTK787/ZK 222584, RPI.4610, squalamine lactate, SU5416, thalidomide, TNP-470, combretastatin, tamoxifen, COL-3, neovastat, BMS-275291, SU6668, anti-VEGF antibody, Medi-522 (Vitaxin II), CAI, Interleukin-12, IM862, Amilloride, Angiostatin®Protein, Angiostatin K1-3, Angiostatin K1-5, Captopril, DL-alpha-Difluoromethylomithine, DL-alpha-Difluoromethylornithine HCl, His-Tag® EndostatinTMProtein, Fumagillin, Herbimycin A, 4-Hydroxyphenylretinamide, Juglone, Laminin, Laminin Hexapeptide, Laminin Pentapeptide, Lavendustin A, Medroxyprogesterone, Medroxyprogesterone Acetate, Minocycline, Minocycline HCl, Placental Ribonuclease Inhibitor, Suramin, Sodium Salt Suramin, Human Platelet Thrombospondin, Neutrophil Granulocyte, monoclonal antibodies directed against specific proangiogenic factors and/or their receptors (e.g. Avastin, Erbitux, Vectibix, Herceptin); small molecule tyrosine kinase inhibitors of multiple proangiogenic growth factor receptors (e.g. Tarceva, Nexavar, Sutent, Iressa); inhibitors of mTOR (mammalian target of rapamycin) (e.g. Torisel); interferon alpha, beta and gamma; IL-12; matrix metalloproteinases (MMP) inhibitors (e.g. COL3, Marimastat, Batimastat); EMD121974 (Cilengitide); Vitaxin; Squalamin; COX-2 inhibitors; PDGFR inhibitors (e.g., Gleevec); NM3 and 2-ME2.

According to some embodiments, the anti-angiogenesis agent is paclitaxel.

According to some embodiments, the polymeric backbone is derived from N-(2-hydroxyprpyl)methacrylamide (HPMA).

According to an aspect of embodiments of the invention there is provided a conjugate comprising a polymeric backbone having attached thereto an anti-angiogenesis agent and a bisphosphonate bone targeting moiety.

According to some embodiments, at least one of the anti-angiogenesis agent and the bone targeting moiety is attached to the polymeric backbone via a linker.

According to some embodiments, the linker is a biodegradable linker.

According to some embodiments, each of the anti-angiogenesis agent and the bone targeting moiety is attached to the polymeric backbone via a linker.

According to some embodiments, the bisphosphonate moiety is selected from a group consisting of alendronate, cimadronate, clodronate, tiludronate, etidronate, ibandronate, neridronate, olpadronate, risedonate, piridronate, pamidronate and zoledronate.

According to some embodiments, the bisphosphonate is alendronate.

According to some embodiments, the biodegradable linker is selected from the group consisting of a pH-sensitive linker and an enzymatically-cleavable linker.

According to some embodiments, the biodegradable linker is an enzymatically-cleavable linker.

According to some embodiments, the enzymatically-cleavable linker is cleaved by an enzyme which is expressed in tumor tissues.

According to some embodiments, the enzymatically-cleavable linker is cleaved by an enzyme which is overexpressed in tumor tissues.

According to some embodiments, the enzyme is selected from a group consisting of Cathepsin B, Cathepsin K, Cathepsin D, Cathepsin H, Cathepsin L, legumain, MMP-2 and MMP-9.

According to some embodiments, the biodegradable linker comprises an oligopeptide having from 2 to 10 amino acid residues.

According to some embodiments, the oligopeptide is selected from the group consisting of -[Ala-Leu-Ala]-(SEQ ID NO:4), -[Cit-Val]- (SEQ ID NO:5), -[Gly-Leu-Gly]- (SEQ ID NO:6), -[Gly-Phe-Gly]- (SEQ ID NO:7), -[Gly-Leu-Phe-Gly]- (SEQ ID NO:8), -[Gly-Phe-Leu-Gly]- (SEQ ID NO:3), -[Ala-Leu-Ala-Leu]- (SEQ ID NO:9), -[Phe-Lys]- (SEQ ID NO:10), and -[Gly-Phe-Leu-Gly-Phe-Lys]- (SEQ ID NO:11).

According to some embodiments, the anti-angiogenesis agent is attached to the polymeric backbone via a linker that comprises the -[Gly-Phe-Leu-Gly-Phe-Lys] (SEQ ID NO:11).

According to some embodiments, the bone targeting moiety is attached to the polymeric backbone via a linker that comprises the -[Gly-Phe-Leu-Gly]- (SEQ ID NO:3).

According to some embodiments, the conjugate further comprising a spacer linking the anti-angiogenesis agent and/or the bisphosphonate to the polymeric backbone and/or to the linker.

According to some embodiments, the anti-angiogenesis agent is paclitaxel and the spacer links the paclitaxel to the polymeric backbone or to the biodegradable linker.

According to some embodiments, the spacer is degradable.

According to some embodiments, the spacer is p-aminobenzyl carbonate (PABC).

According to some embodiments, the conjugate has the general formula II, as defined herein.

According to some embodiments, the conjugate further comprising a labeling agent attached thereto.

According to some embodiments, the labeling agent is selected from the group consisting of a fluorescent agent, a radioactive agent, a magnetic agent, a chromophore, a bioluminescent agent, a chemiluminescent agent, a phosphorescent agent and a heavy metal cluster.

According to an aspect of embodiments of the invention there is provided a pharmaceutical composition comprising, as an active ingredient, the conjugate as described herein and a pharmaceutically acceptable carrier.

According to some embodiments, the composition is packaged in a packaging material and identified in print, in or on the packaging material, for use in the treatment of a bone related disease or disorder.

According to some embodiments, the conjugate comprises a labeling agent, the composition being packaged in a packaging material and identified in print, in or on the packaging material, for use in monitoring a bone related disease or disorder.

According to an aspect of some embodiments of the invention there is provided a method of treating a bone related disease or disorder in a subject in need thereof, the method comprising administering to the subject a therapeutically effective amount of the conjugate as described herein.

According to an aspect of some embodiments of the invention there is provided a method of monitoring a bone related disease or disorder in a subject, the method comprising: administrating to the subject the conjugate having a labeling agent attached thereto, as described herein; and employing an imaging technique for monitoring a distribution of the conjugate within the body or a portion thereof.

According to an aspect of some embodiments of the invention there is provided of the conjugate as described herein as a medicament.

According to an aspect of some embodiments of the invention there is provided a use of the conjugate as described herein in the manufacture of a medicament for treating a bone-related disease or disorder.

According to an aspect of some embodiments of the invention there is provided of the conjugate as described herein, having a labeling agent attached thereto as a diagnostic agent.

According to an aspect of some embodiments of the invention there is provided a of the conjugate having a labeling agent attached thereto, as described herein, in the manufacture of a diagnostic agent for monitoring a bone related disease or disorder.

According to some embodiments, the disease or disorder is associated with angiogenesis.

According to some embodiments, the disease or disorder is selected from the group consisting of bone metastases and bone cancer.

According to an aspect of some embodiments of the invention there is provided a process of preparing the conjugate as described herein, the process comprising:

(a) co-polymerizing a plurality of monomeric units of the polymeric backbone, wherein a portion of the plurality comprises monomeric units terminating by a first reactive group, and another portion of the plurality comprises monomeric units terminating by a second reactive group, to thereby obtain a co-polymer comprising a polymeric backbone that comprises a plurality of backbone units, wherein a portion of the backbone units has the first reactive group and another portion of the backbone units has the second reactive group, the first reactive group being capable of reacting with the anti-angiogenesis agent and the second reactive being capable of reacting with the bisphosphonate;

(b) reacting the co-polymer with the anti-angiogenesis agent or with a derivative thereof, via the first reactive group, to thereby obtain the co-polymer having the anti-angiogenesis agent attached thereto; and (c) reacting the co-polymer with the bisphosphonate or a derivative thereof, via the second reactive group, to thereby obtain the co-polymer having the bisphosphonate attached thereto, thereby obtaining the conjugate.

According to some embodiments, (b) is performed subsequent to, concomitant with or prior to (c).

According to some embodiments, the monomeric units terminating by the first reactive group and/or the monomeric units terminating by the second reactive group further comprise a linker, the linker terminates by the first reactive group or by the second reactive group.

According to some embodiments, the process further comprising, prior to (a), attaching the linker to the monomeric units.

According to some embodiments, at least one of the anti-angiogenesis agent and the bisphosphonate is linked to the polymeric backbone and/or to the linker via a spacer, the process further comprising, prior to (a), attaching the spacer to at least one of the portions of the monomeric units.

According to some embodiments, at least one of the anti-angiogenesis agent and the bisphosphonate is linked to the polymeric backbone and/or to the linker via a spacer, the process further comprising, prior to (a), attaching the spacer to the anti-angiogenesis agent and/or to the bisphosphonate, to thereby obtain the derivative of the anti-angiogenesis agent and/or of the bisphosphonate.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 presents a scheme illustrating the mechanism for the enzymatic cleavage of a HPMA copolymer-PTX-FK-ALN conjugate (Compound 1; SEQ ID NO:12) according to some embodiments of the invention, by cathepsin B.

Figure 2A:
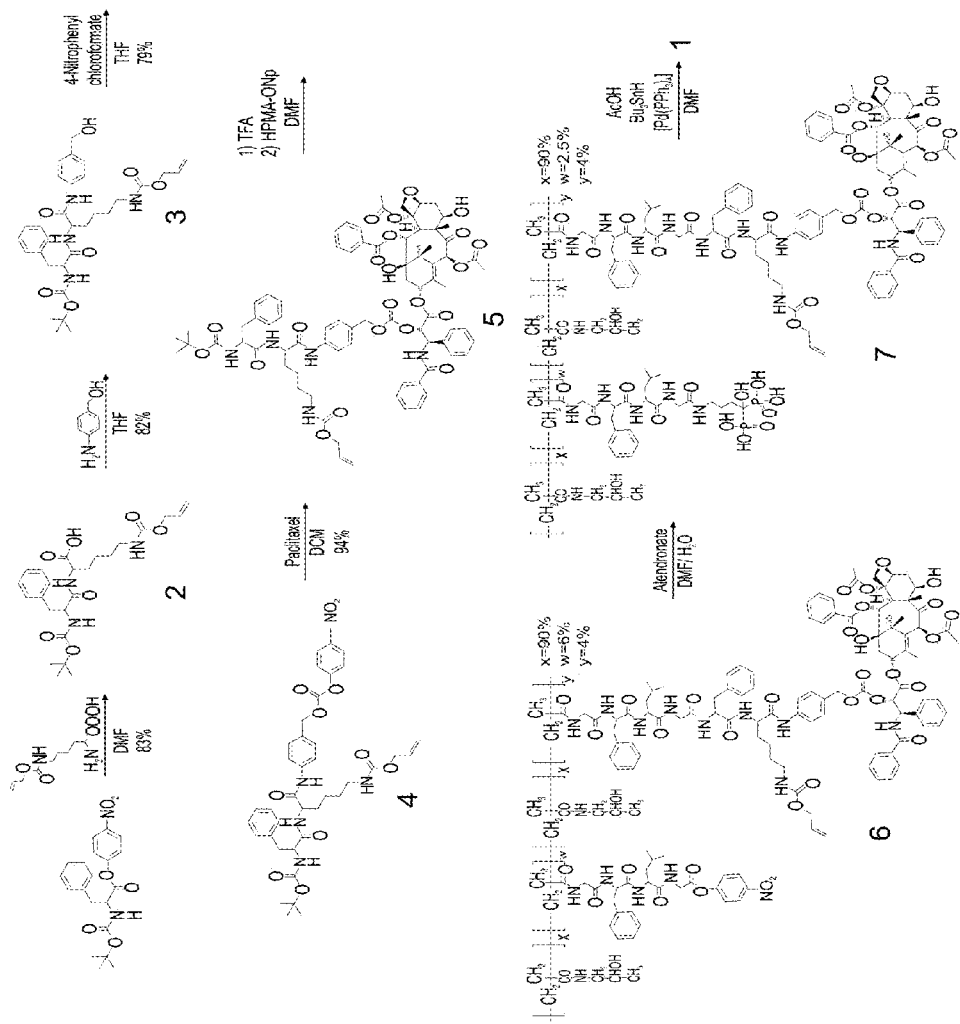
Figure 2B:
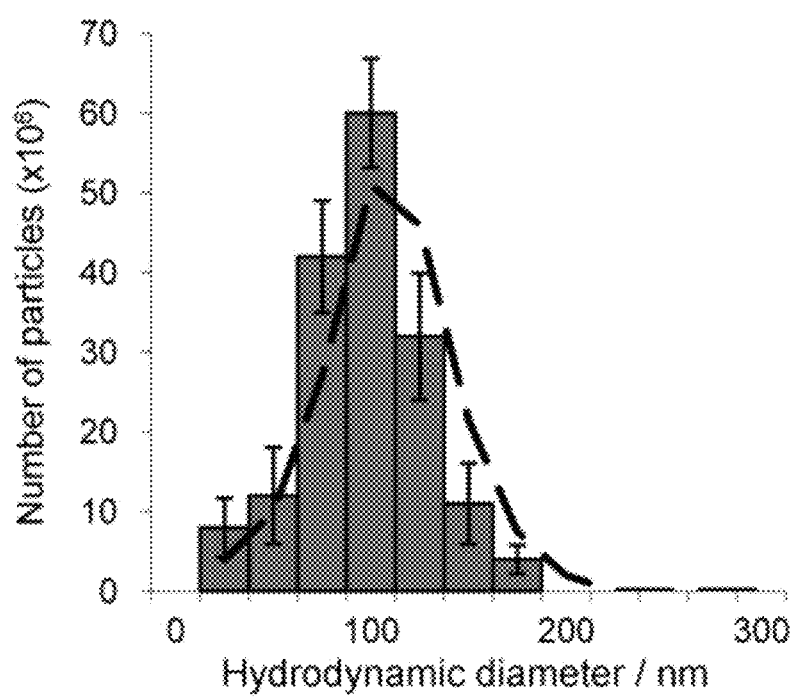
Figure 2C:
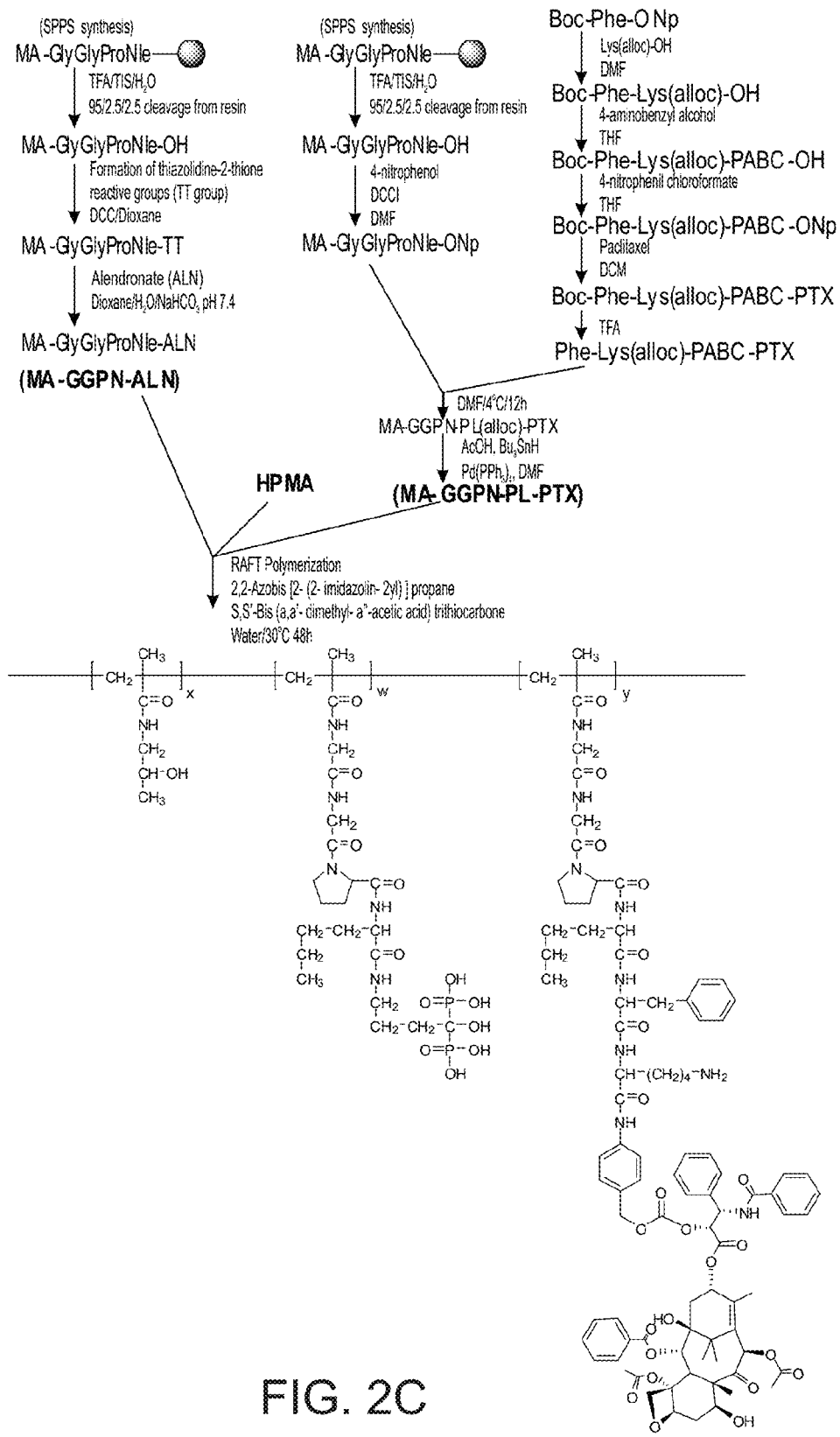

FIGS. 2A-C present a scheme illustrating the synthesis of an HPMA copolymer-PTX-FK-ALN conjugate (Compound 1; SEQ ID NO:12) according to some embodiments of the invention (FIG. 2A), and the hydrodynamic diameter and size distribution of the conjugate (FIG. 2B), and a scheme illustrating the synthesis of another HPMA copolymer-PTX-ALN conjugate (SEQ ID NO:12), via RAFT, according to some embodiments of the invention (FIG. 2C).

Figure 3A:
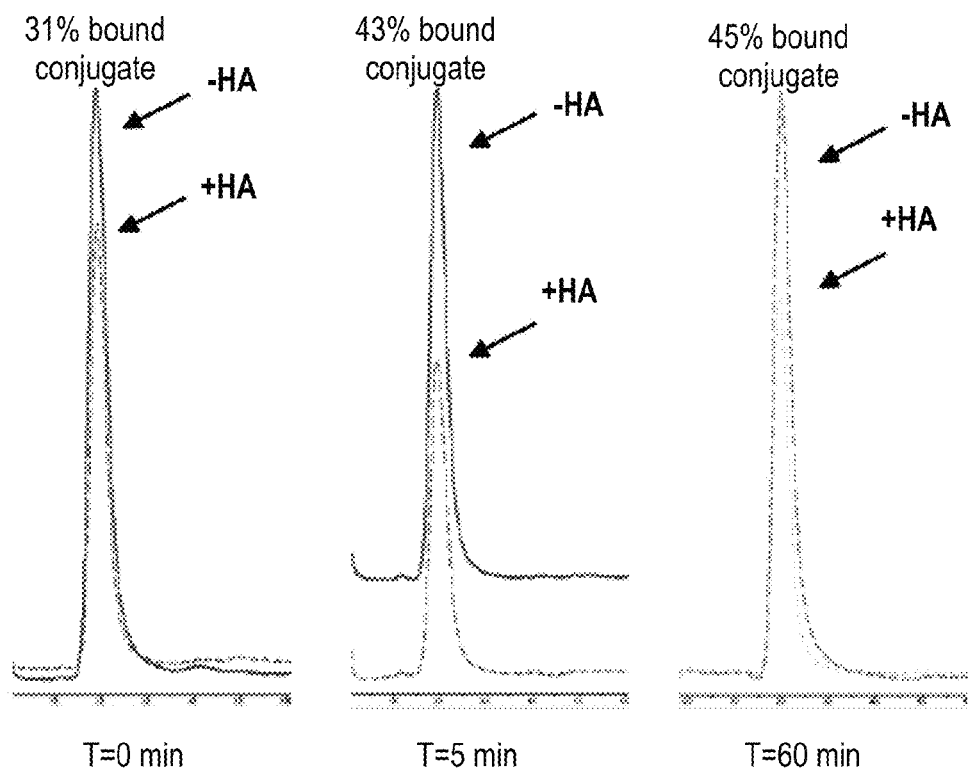
Figure 3B:
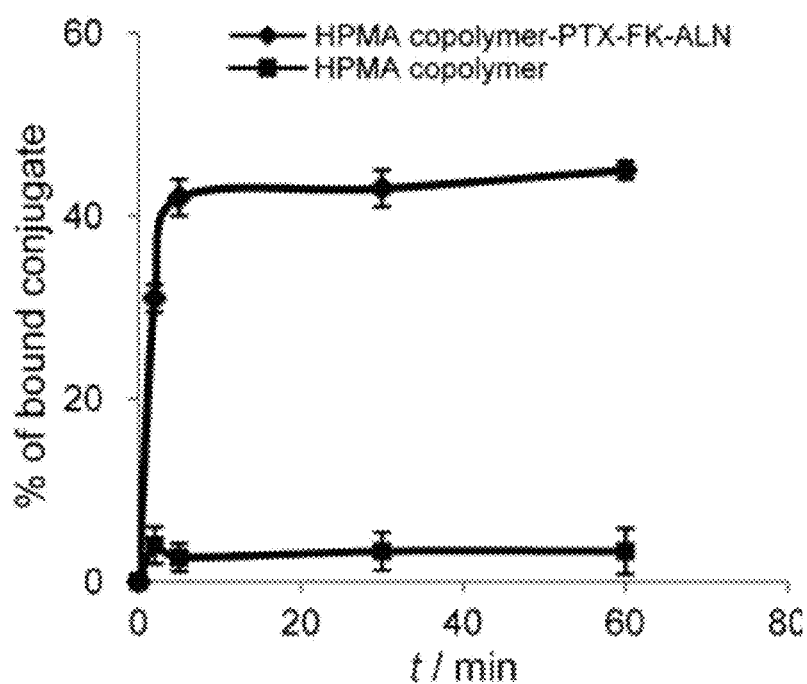

FIGS. 3A-B present the FPLC detection of unbound HPMA copolymer-paclitaxel-FK-ALN conjugate (SEQ ID NO:12), according to some embodiments of the invention, in tested samples, in the presence and absence of hydroxyapatite, at selected time points (FIG. 3A), and a plot showing the percentages of HPMA-paclitaxel-FK-ALN conjugate (SEQ ID NO:12) bound to hydroxyapatite as a function of the elution time (FIG. 3B). Serving as control is free HPMA copolymer.

Figure 4A:
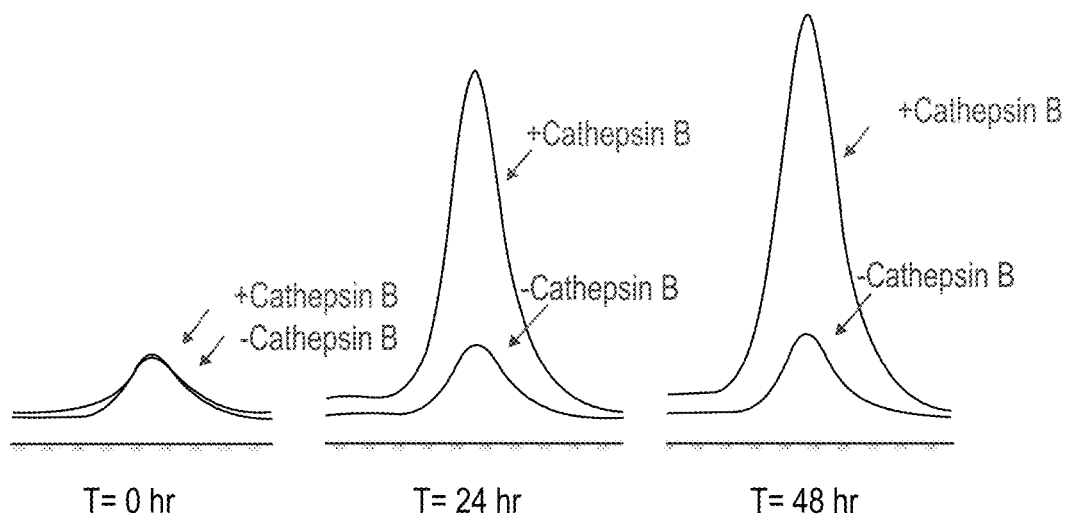
Figure 4B:
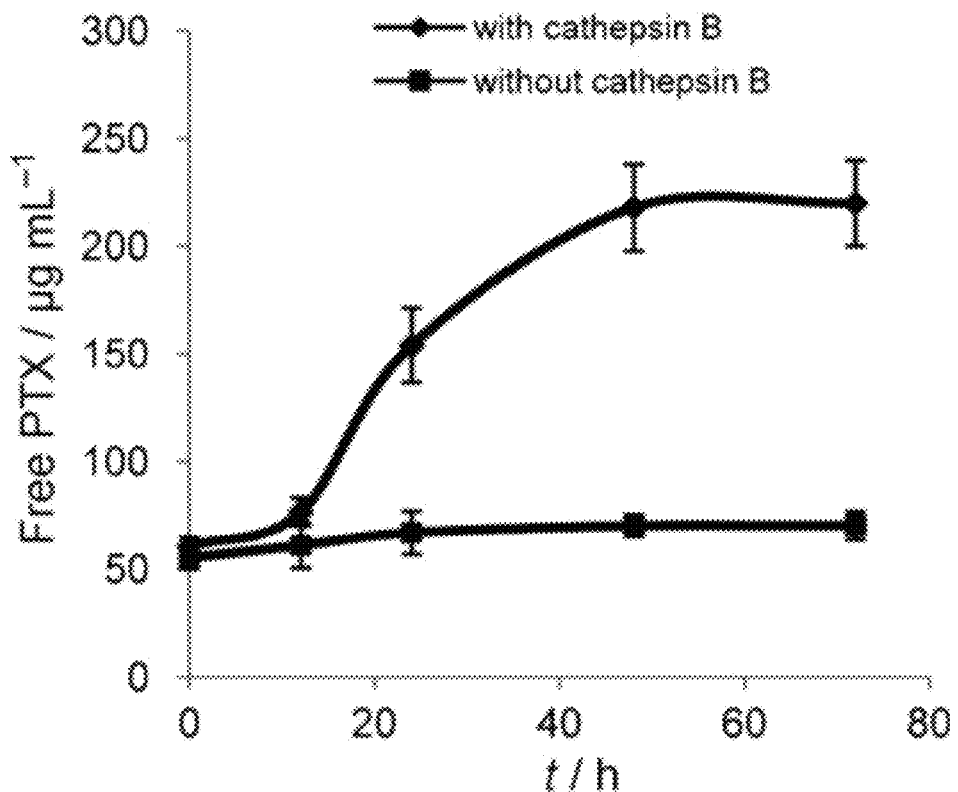

FIGS. 4A-B present HPLC detection of in vitro enzymatically-triggered release of paclitaxel from a HPMA copolymer-PTX-FK-ALN conjugate (SEQ ID NO:12), according to some embodiments of the invention, by cathepsin B, upon 0, 24 and 48 hours incubation of the conjugate at 37° C. in phosphate buffer, in the presence of reduced glutathione and cathepsin B (FIG. 4A), and a plot showing the amount of paclitaxel released from the conjugate (Free PTX) as a function of its incubation time with cathepsin B (FIG. 4B).

Figure 5:
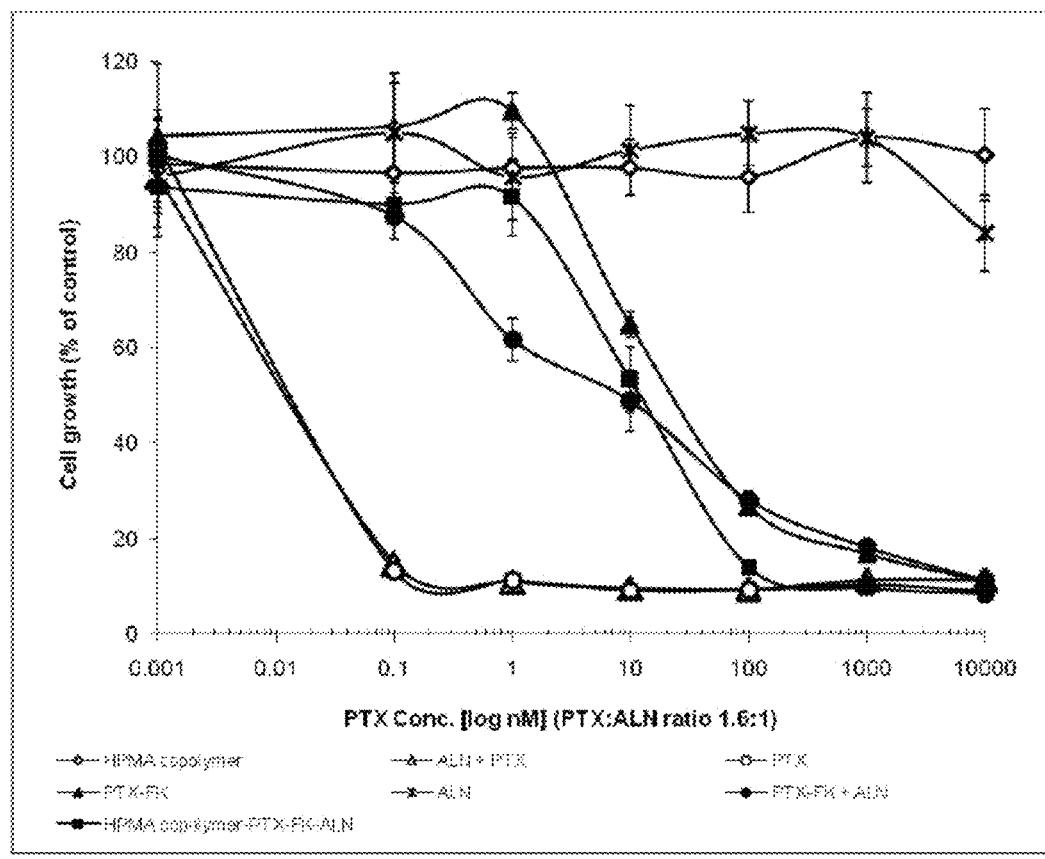

FIG. 5 presents comparative plots demonstrating that paclitaxel retains its anti-angiogenic effect on HUVEC cells when bound to a HPMA copolymer. Results are presented as percents of cell growth (out of the control group) as a function of paclitaxel concentration, for HPMA polymer alone (blank diamonds); free paclitaxel-FK (PTX-FK; SEQ ID NO:13) (full triangles); HPMA copolymer-PTX-FK-ALN conjugate (SEQ ID NO: 12), according to some embodiments of the present invention (full squares); a combination of free paclitaxel+free ALN (ALN+PTX; blank triangles); free ALN (crosses); free paclitaxel (PTX, blank circles); and a combination of free paclitaxel-FK (SEQ ID NO: 13)+free ALN (PTX-FK+ALN; filled circles).

FIGS. 6A-C present the 2-D chemical structure of a non-cleavable HPMA-GGGG-PTX conjugate (SEQ ID NO: 14) (FIG. 6A), a cathepsin B-enzymatically cleavable HPMA-GGFK-PTX conjugate (SEQ ID NO: 15) (FIG. 6B), and a comparative plot showing that a control, non-cleavable, HPMA-GGGG-PTX conjugate (SEQ ID NO: 14) is less active than the cathepsin B-cleavable HPMA GGFK-PTX conjugate (SEQ ID NO: 15) in inhibiting HUVEC proliferation (FIG. 6C). HUVEC were incubated with HPMA-GGGG-PTX (SEQ ID NO: 14) (close triangle) or with HPMA-GGFK-PTX (SEQ ID NO: 15) (close square) conjugates for 48 hours. HPMA-GGGG-PTX conjugate (SEQ ID NO: 14) inhibited the proliferation of HUVEC at a 2-logs higher concentration than the cathepsin B cleavable HPMA-GGFK-PTX conjugate (SEQ ID NO: 15). Data represents mean±SD. X axis in logarithmic scale.

Figure 7:
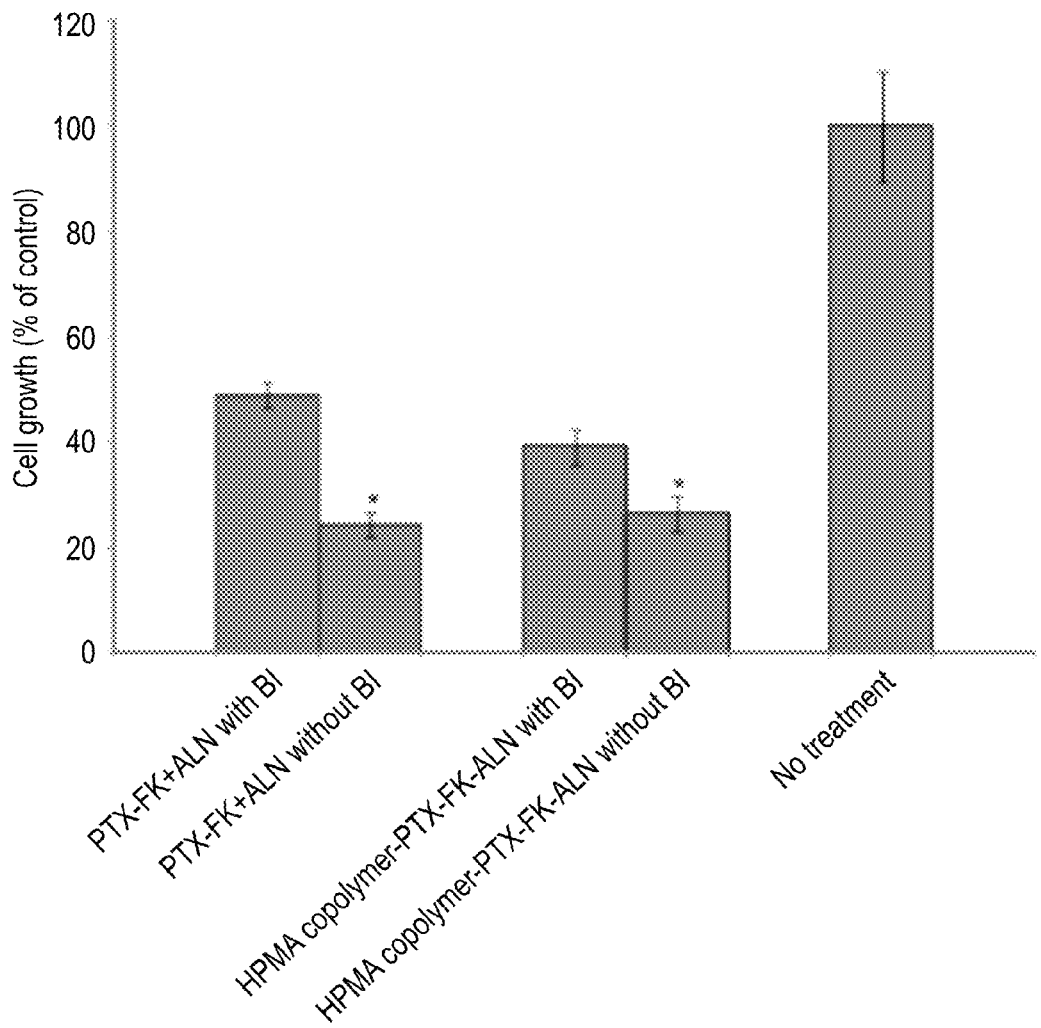

FIG. 7 presents a bar graph showing that in the presence of a Cathepsin B inhibitor the cytotoxicity of a HPMA copolymer-PTX-FK-ALN conjugate (SEQ ID NO: 12), according to some embodiments of the invention, and of PTX-FK (SEQ ID NO:13) is reduced. HUVECs were incubated with HPMA copolymer-PTX-FK-ALN conjugate (SEQ ID NO: 12) or with PTX-FK (SEQ ID NO: 13)+ALN, at equivalent concentrations of 500 nM and 300 nM respectively, in the presence or absence of a cathepsin B inhibitor (BI) for 48 hours. HUVEC not incubated with any drug served as control (denoted as "no treatment"). Results are presented as percents of cell growth (out of the control group). Data represents mean±SD. *=p<0.05.

Figure 8:
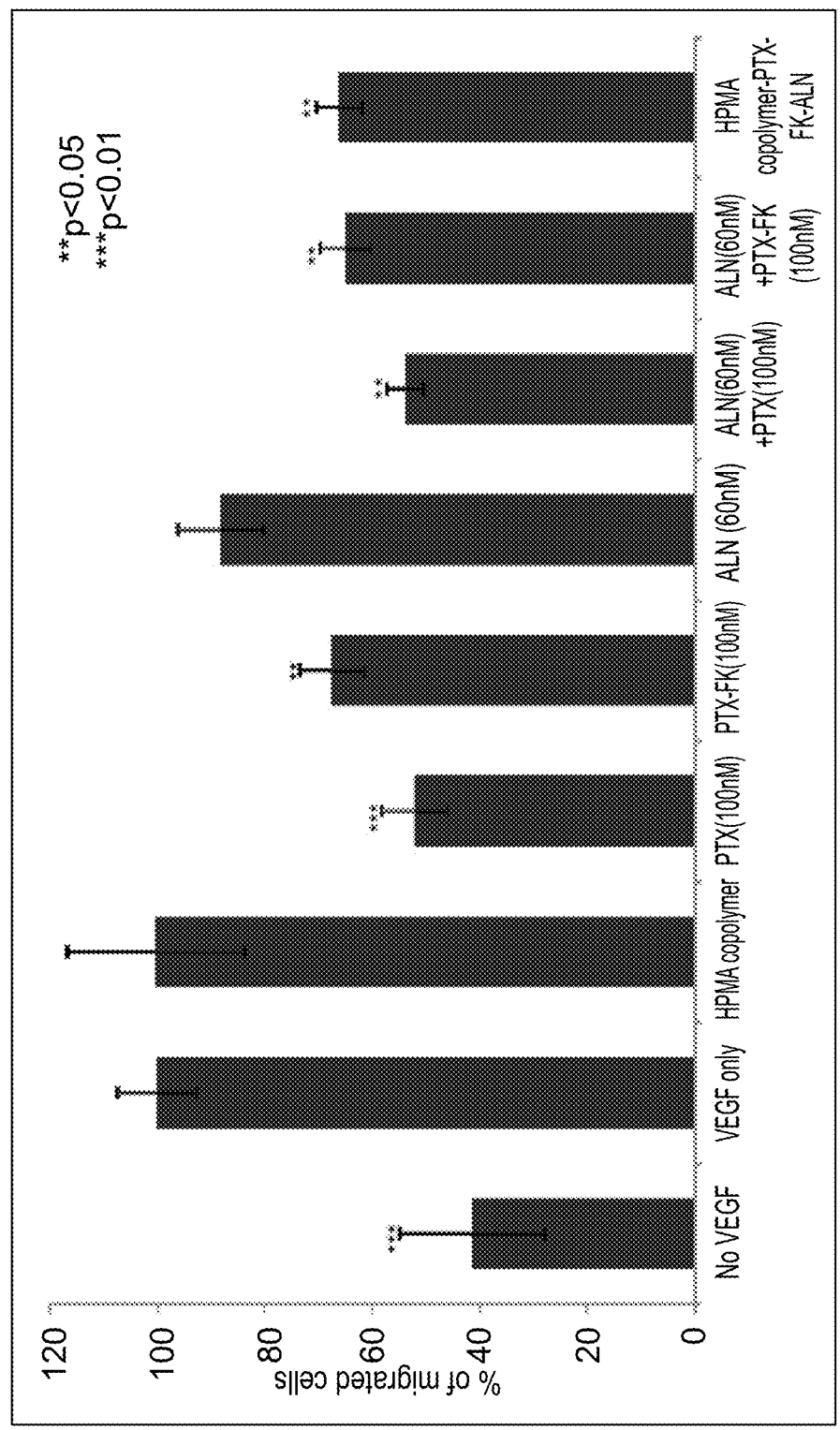

FIG. 8 presents a bar graph showing the inhibition of the migration of HUVECs towards the chemoattractant VEGF by a HPMA copolymer-PTX-FK-ALN conjugate (SEQ ID NO: 12), according to some embodiments of the invention. HUVECs were incubated with a combination of Paclitaxel and ALN, a combination of Paclitaxel-FK (SEQ ID NO: 13) and ALN, with each drug alone, and with HPMA copolymer-Paclitaxel-FK-ALN conjugate (SEQ ID NO: 12). Migration toward VEGF was measured and normalized to percent migration with 100% representing migration to VEGF alone.

Figure 9A:
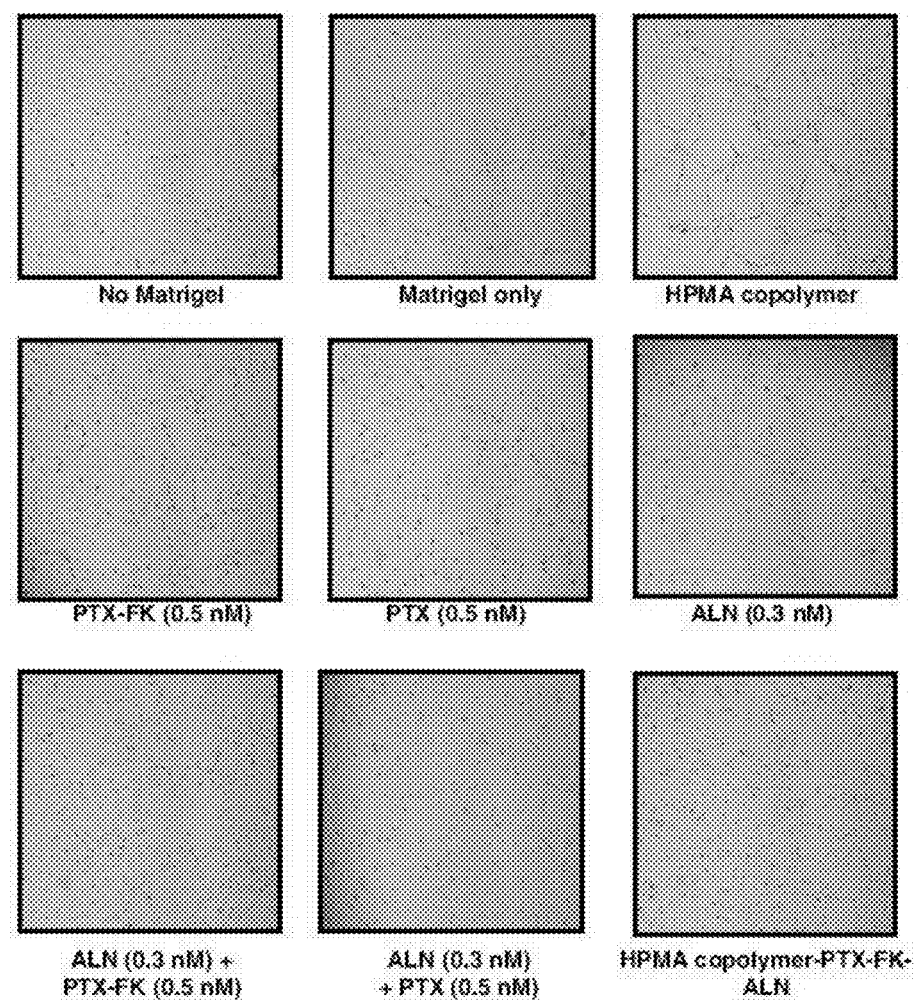
Figure 9B:
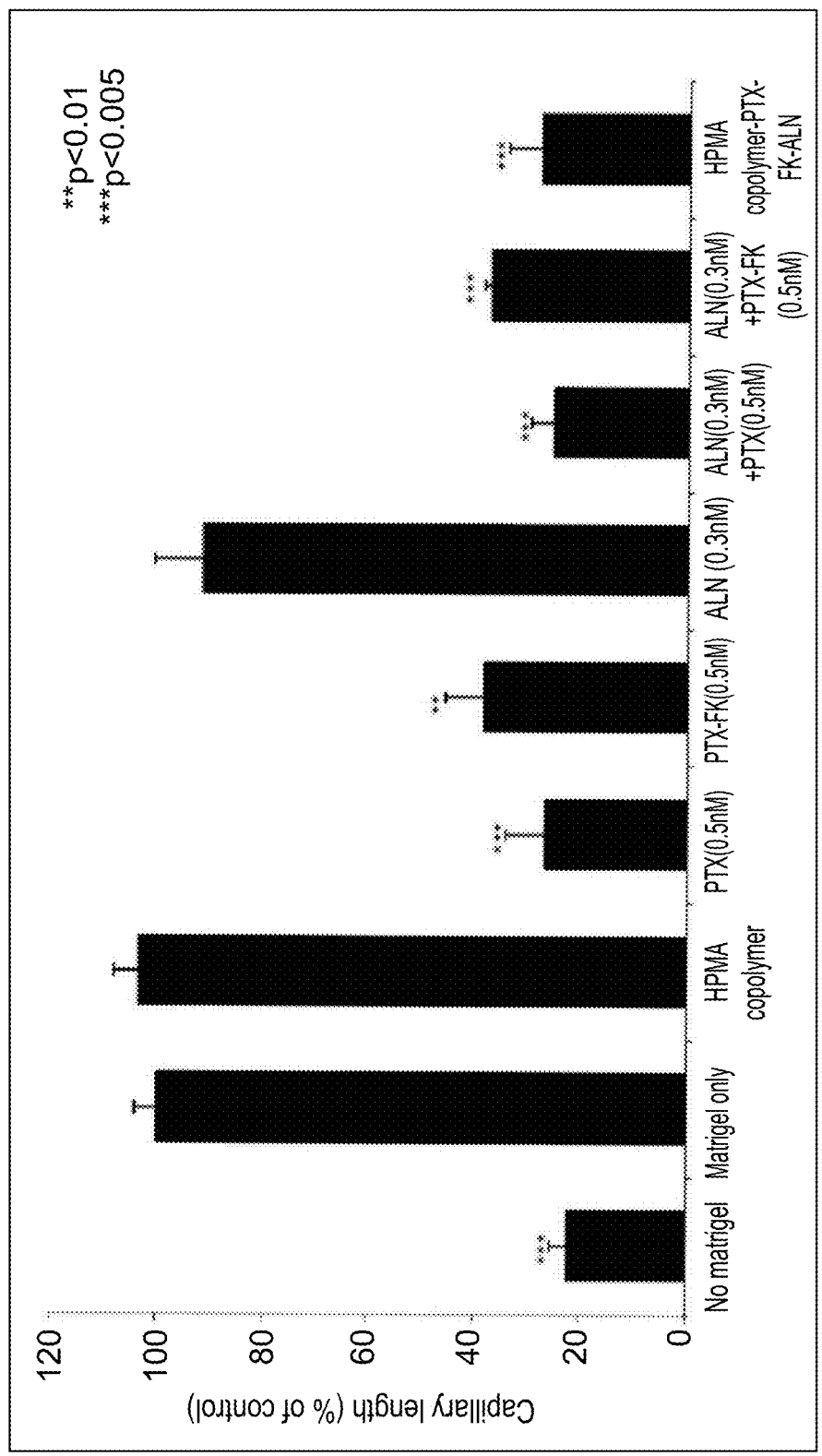

FIGS. 9A-B present images (FIG. 9A) and a bar graph (FIG. 9B) showing the effect of a HPMA copolymer-PTX-FK-ALN conjugate (SEQ ID NO: 12), according to some embodiments of the invention, free paclitaxel-FK (PTX; SEQ ID NO:13) free ALN and a mixture thereof on the ability of HUVECs to form capillary-like tube structures upon 8 hours incubation (FIG. 9A) and the percentages of inhibition of HUVEC capillary-like tube structures by the different concentrations of the tested agent (FIG. 9B).

Figure 10:
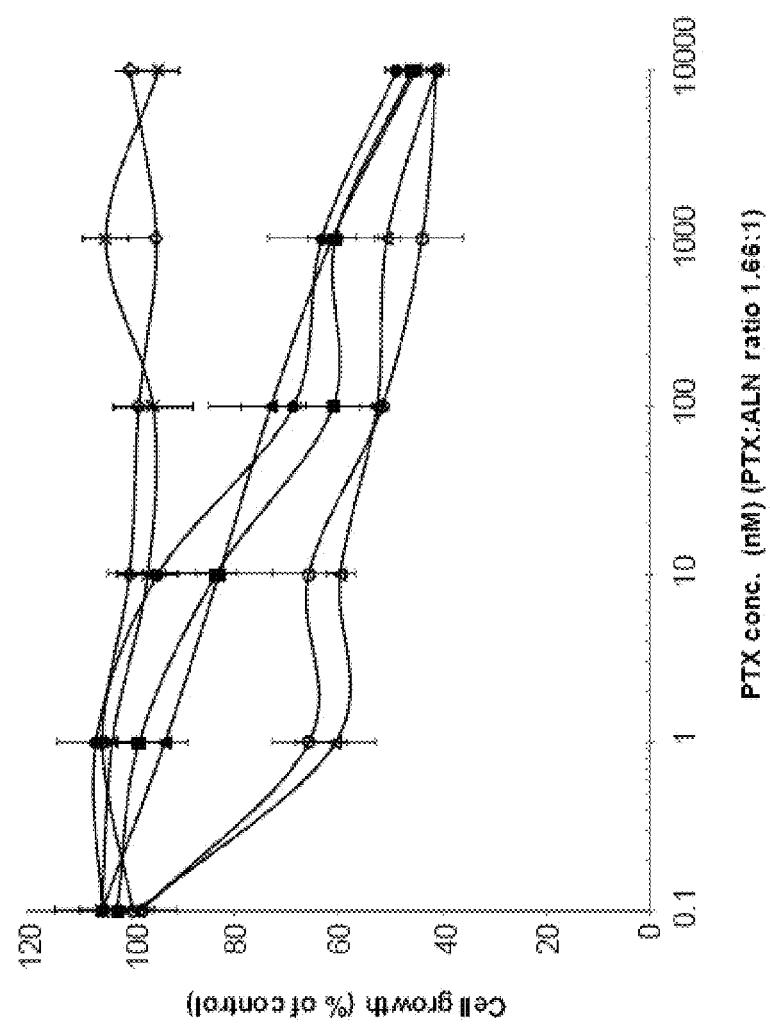

FIG. 10 presents comparative plots demonstrating that paclitaxel retains its cytotoxic effect on human prostate cancer cells (PC3) when bound to the HPMA copolymer. Results are presented as percents of cell growth (out of the control group) as a function of paclitaxel concentration. PC3 cells were incubated with PTX (open circle), ALN (cross), PTX-FK (close triangle; SEQ ID NO: 13), ALN+PTX (open triangle), PTX-FK (SEQ ID NO: 13)+ALN (close circle), HPMA copolymer (open diamond), and HPMA copolymer-PTX-FK-ALN conjugate (SEQ ID NO: 12; close square) for 72 hours. Data represents mean±SD. X axis in logarithmic scale.

Figure 11A:
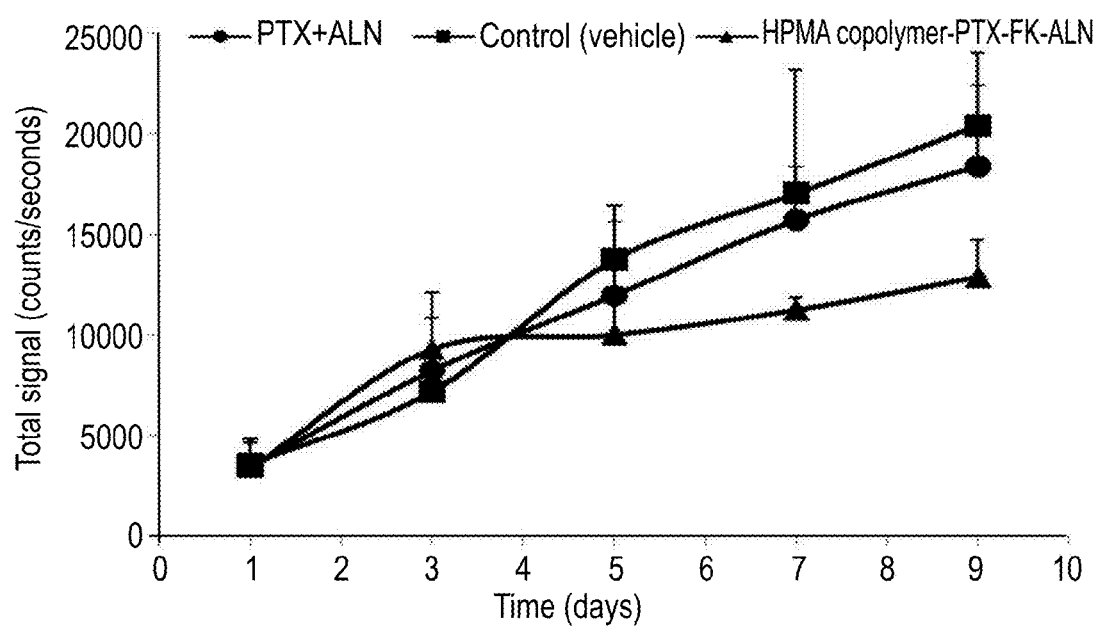
Figure 11B:
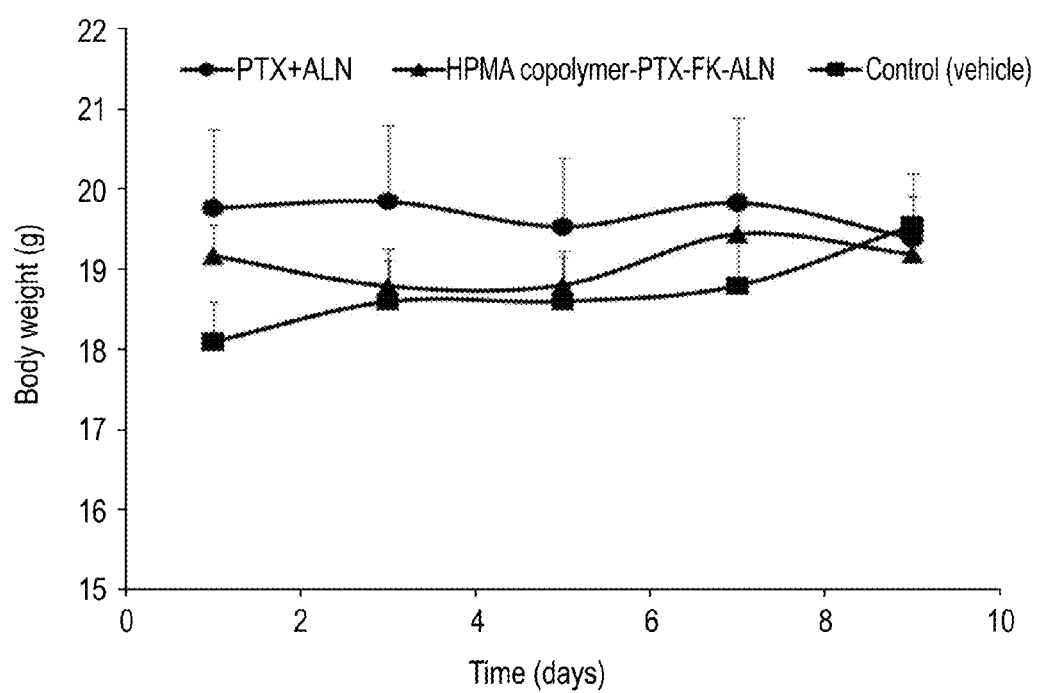

FIGS. 11A-B present comparative plots demonstrating that HPMA copolymer-Paclitaxel-FK-ALN conjugate (SEQ ID NO: 12), according to some embodiments of the present invention, inhibits DA3 tumors in the tibia (FIG. 11A) and that no body weight loss was observed in the treated mice (FIG. 11B). Antitumor effect of free (closed circles) or conjugated (closed triangles) ALN and PTX on DA3 tumor growth was compared with vehicle-treated control group (closed squares). Tumor progression was assessed using intravital non-invasive fluorescence imaging of mCherry-labeled DA3 tumor-bearing mice. 9 days following treatment initiation a HPMA copolymer-PTX-FK-ALN conjugate (SEQ ID NO: 12) inhibited tumor growth by 37% while no significant change in tumor growth was observed in the mice treated with combined free ALN+free PTX and in the control group (FIG. 11A). Body weight of treated mice was monitored and no body weight loss was observed in any of the groups (FIG. 11B).

DESCRIPTION OF SPECIFIC EMBODIMENTS OF THE INVENTION

The present invention, in some embodiments thereof, relates to chemical conjugates and their use in therapy and diagnosis and, more particularly, but not exclusively, to chemical conjugates of a polymer having attached thereto an anti-angiogenesis agent and a bone targeting moiety, which are useful in the treatment and monitoring of bone related diseases and disorders such as bone cancer and bone metastases.

The principles and operation of the conjugates, compositions, use, methods and processes according to the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, currently known agents for treating bone related cancer and other angiogenesis-related conditions, at doses where anti-tumor activity is achieved, are characterized by high toxicity, which limits their use.

The present inventors have now devised and successfully prepared and practiced novel conjugates of a copolymer having attached thereto an anti-angiogenesis agent and a bone targeting moiety being a bisphosphonate.

While the described agents are designed so as to exhibit an anti-angiogenesis activity beneficial for treating bone cancer or bone metastases, such an improved specificity is achieved by both an EPR effect induced by the polymer and the targeting effect induced by the bone targeting moiety.

As demonstrated in the Examples section that follows, the present inventors have successfully prepared and practiced a novel conjugate of a hydroxypropyl methacrylamide (HPMA) co-polymer, having attached thereto the anti-angiogenesis agent Paclitaxel and the bisphosphonate alendronate (ALN) wherein the Paclitaxel and the alendronate are conjugated to the HPMA-derived polymeric backbone via biodegradable linkers (HPMA copolymer-paclitaxel-FK-ALN; (SEQ ID NO: 12) see, FIG. 2). The anti-angiogenesis activity of the conjugate has been demonstrated by the ability to inhibit the proliferation of HUVEC by the conjugate (FIG. 5), the ability to inhibit of vascular endothelial growth factor (VEGF)-induced HUVEC migration (FIG. 8) and the ability to inhibit HUVEC formation of capillary-like tube structures (FIG. 9). The binding capacity of the conjugate to bone mineral was further demonstrated using an in vitro hydroxyapatite binding assay with 50% of the conjugate being bound to hydroxyapatite (FIG. 3). Additionally, the cytotoxic activity of the conjugate on the proliferation of the human prostate PC3 cell line was shown (FIG. 10). In vivo experiments pointed to the beneficial activity of the conjugate as compared to the free Paclitaxel agent whereby a very aggressive tumor model being DA3 murine mammary cancer injected intra-tibia, was unaffected by free PTX treatment whereas 37% of tumor growth was inhibited by HPMA copolymer-PTX-FK-ALN conjugate (SEQ ID NO: 12) treatment (FIG. 11).

These results demonstrate that the conjugates described herein can be beneficially used for treating bone and bone related disorders (such as cancer and disorders characterized by angiogenesis).

According to an aspect of some embodiments of the present invention there is provided a polymeric conjugate comprising a polymeric backbone having attached thereto at least one anti-angiogenesis agent and at least one bone targeting moiety, the bone targeting moiety being a bisphosphonate.

The term "anti-angiogenesis agent", which is also referred to herein, interchangeably as "anti-angiogenic agent" or "angiogenesis inhibitor", describes an agent having the ability to (a) inhibit endothelial cell proliferation or migration, (b) kill proliferating endothelial cells, and/or (c) inhibit the formation of new blood vessels in a tissue.

Exemplary anti-angiogenesis agents that are suitable for use in the context of embodiments of the invention include, but are not limited to, paclitaxel, 2-methoxyestradiol, prinomastat, batimastat, BAY 12-9566, carboxyamidotriazole, CC-1088, dextromethorphan acetic acid, dimethylxanthenone acetic acid, endostatin, IM-862, marimastat, a matrix metalloproteinase, penicillamine, PTK787/ZK 222584, RPI.4610, squalamine lactate, SU5416, thalidomide, TNP-470, combretastatin, tamoxifen, COL-3, neovastat, BMS-275291, SU6668, anti-VEGF antibody, Medi-522 (Vitaxin II), CAI, Interleukin-12, IM862, Amilloride, Angiostatin®Protein, Angiostatin K1-3, Angiostatin K1-5, Captopril, DL-alpha-Difluoromethylornithine, DL-alpha-Difluoromethylornithine HCl, His-Tag® EndostatinTMProtein, Fumagillin, Herbimycin A, 4-Hydroxyphenylretinamide, Juglone, Laminin, Laminin Hexapeptide, Laminin Pentapeptide, Lavendustin A, Medroxyprogesterone, Medroxyprogesterone Acetate, Minocycline, Minocycline HCl, Placental Ribonuclease Inhibitor, Suramin, Sodium Salt Suramin, Human Platelet Thrombospondin, Neutrophil Granulocyte, monoclonal antibodies directed against specific proangiogenic factors and/or their receptors (e.g. Avastin, Erbitux, Vectibix, Herceptin); small molecule tyrosine kinase inhibitors of multiple proangiogenic growth factor receptors (e.g. Tarceva, Nexavar, Sutent, Iressa); inhibitors of mTOR (mammalian target of rapamycin) (e.g. Torisel); interferon alpha, beta and gamma; IL-12; matrix metalloproteinases (MMP) inhibitors (e.g. COL3, Marimastat, Batimastat); EMD121974 (Cilengitide); Vitaxin; Squalamin; COX-2 inhibitors; PDGFR inhibitors (e.g., Gleevec); NM3 and 2-ME2.

As used herein, the term "COX-2 inhibitor" refers to a non-steroidal drug that relatively inhibits the enzyme COX-2 in preference to COX-1. Preferred examples of COX-2 inhibitors include, but are no limited to, celecoxib, parecoxib, rofecoxib, valdecoxib, meloxicam, and etoricoxib.

In some embodiments, the anti-angiogenesis agents is selected from the group consisting of TNP-470, Paclitaxel, monoclonal antibodies directed against specific proangiogenic factors and/or their receptors (e.g. Avastin, Erbitux, Vectibix, Herceptin); small molecule tyrosine kinase inhibitors of multiple proangiogenic growth factor receptors (e.g. Tarceva, Nexavar, Sutent, Iressa); inhibitors of mTOR (mammalian target of rapamycin) (e.g. Torisel); interferon alpha, beta and gamma; IL-12; matrix metalloproteinases (MMP) inhibitors (e.g. COL3, Marimastat, Batimastat); EMD121974 (Cilengitide); Vitaxin; Squalamin; COX-2 inhibitors; PDGFR inhibitors (e.g., Gleevec); NM3; and 2-ME2.

In some embodiments, the anti-angiogenesis agent is Paclitaxel.

The microtubule-interfering agent Paclitaxel is a drug commonly used for the treatment of advanced metastatic breast cancer. However, it is neurotoxic, it causes hematological toxicity and many breast tumors develop resistance thereto. It has been recently shown that Paclitaxel at ultra low doses inhibits angiogenesis. However, Paclitaxel is poorly soluble and the excipients Cremophor EL or ethanol used today to solubilize its commercial form, cause hypersensitivity reactions.

It is noted herein that while some anti-angiogenesis agents exhibit an anti-neoplastic activity, embodiments of the invention encompass those anti-neoplastic agents that can act via angiogenesis inhibition.

The phrase "bone targeting moiety", as used herein, describes a moiety that is capable of preferentially accumulating in hard tissues (i.e. bone tissues) rather than any other organ or tissue, after administration in vivo.

Bisphosphonates (BPs) such as alendronate are compounds with a chemical structure similar to that of inorganic pyrophosphate (PPi), an endogenous regulator of bone mineralization. The pharmacokinetic profile of bisphosphonates, which exhibit a strong affinity to bone mineral under physiological conditions, their low toxicity and anti-angiogenic activity (typically exhibited at relatively high concentration thereof) are advantageous for targeting to tumors confined to bony tissues.

Accordingly, the bone targeting moiety described herein is a compound which comprises at least two phosphonate ($-P(=O)(OH)_2$) groups, and optionally other functional groups.

Exemplary compounds have the following general formula:

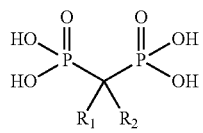

or a pharmaceutically acceptable salt thereof, as defined herein, wherein $R_1$ and $R_2$ are each independently selected from the group consisting of hydrogen, substituted or unsubstituted alkyl, substituted or unsubstituted cycloalkyl, substituted or unsubstituted aryl, substituted or unsubstituted heteroaryl, substituted or unsubstituted heteroalicyclic, halo, hydroxy, thiol, alkoxy, thioalkoxy, aryloxy, and thioaryloxy, as defined hereinbelow.

In some embodiments, at least one of $R_1$ and $R_2$ is an alkyl, cycloalkyl, aryl, heteroaryl or heteroalicyclic, optionally substituted as defined herein.

In some embodiments, the alkyl, cycloalkyl, aryl, heteroaryl or heteroalicyclic is substituted by a reactive group such as amine, hydroxy, thiol, halo, carboxylate, and the like, as defined herein, which enables its conjugation to compatible reactive groups on the polymeric backbone.

In some embodiments, at least one of $R_1$ and $R_2$ is hydroxy and the other one is an alkyl, cycloalkyl, aryl, heteroaryl or heteroalicyclic, as described herein.

In some embodiments, $R_1$ is hydroxy and $R_2$ is an alkyl terminating with an amino group. The alkyl can have from 1 to 6 carbon atoms in its backbone chain.

Exemplary bisphosphonate bone targeting moieties that are suitable for use in the context of embodiments of the invention include, but are not limited to, alendronate, cimadronate, clodronate, tiludronate, etidronate, ibandronate, neridronate, olpadronate, risedronate, piridronate, pamidronate and zoledronate.

In some embodiments the bone targeting moiety is alendronate (4-amino-1-hydroxybutylidene)bisphosphonic acid):

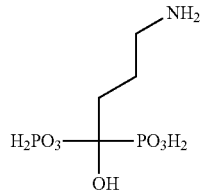

Herein, the terms "alendronate" and "bisphosphonate" encompass any pharmaceutically acceptable salts, solvates and/or hydrates thereof, as defined hereinafter.

As discussed hereinabove, the present inventors have conjugated alendronate to a polymeric backbone together with Paclitaxel and the bone targeting capacity of the obtained polymeric conjugate was demonstrated by the enhanced binding of the conjugate to hydroxyapatite (as a modal mimicking bone tissue) (FIG. 3). The beneficial therapeutic activity of the conjugate in the treatment of a mouse model of bone cancer metastasis was also demonstrated (FIG. 11).

In some embodiments, the polymeric conjugates described herein are composed of a polymeric backbone, formed from a plurality of backbone units that are covalently linked to one another, wherein at least a portion of this plurality of backbone units has an anti-angiogenesis agent, as described herein, attached thereto, and at least another portion of the plurality of backbone units has the bone targeting moiety (the bisphosphonate, as described herein), attached thereto.

Those backbone units that have the anti-angiogenesis agent attached thereto and those backbone units that have the bisphosphonate attached thereto can be randomly dispersed within the polymeric backbone.

The polymeric backbone can further include non-functionalized backbone units, as discussed hereinbelow, to which none of the anti-angiogenesis agent and the bisphosphonate, or any other agent, is attached.

In some embodiments, the polymeric backbone of the conjugates described constitutes polymers (or co-polymers) to which the anti-angiogenesis agent and the bone targeting moiety are attached.

Polymers which are suitable for use in the context of the present embodiments are biocompatible, non-immunogenic and non-toxic. The polymers serve as carriers that enable specific delivery into tumor tissue, possible due to the EPR effect discussed hereinabove.

As used herein, the term "polymer" describes an organic substance composed of a plurality of repeating structural units (backbone units) covalently connected to one another. The term "polymer" as used herein encompasses organic and inorganic polymers and further encompasses one or more of a homopolymer, a copolymer or a mixture thereof (a blend). The term "homopolymer" as used herein describes a polymer that is made up of one type of monomeric units and hence is composed of homogenic backbone units. The term "copolymer" as used herein describes a polymer that is made up of more than one type of monomeric units and hence is composed of heterogenic backbone units. The heterogenic backbone units can differ from one another by the pendant groups thereof.

The polymer is comprised of backbone units formed by polymerizing the corresponding monomeric units whereby the anti-angiogenesis agent and the bone targeting moiety are attached to at least a portion of these backbone units. Some or all of these backbone units are typically functionalized prior to conjugation, so as to have a reactive group for attaching the anti-angiogenesis agent and the bone targeting moiety. Those backbone units that are not functionalized and/or do not participate in the conjugation of the anti-angiogenesis agent and bone targeting moiety are referred to herein as "free" backbone units.

The polymer may be a biostable polymer, a biodegradable polymer or a combination thereof. The term "biostable", as used in this context of embodiments of the invention, describes a compound or a polymer that remains intact under physiological conditions (e.g., is not degraded in vivo).

The term "biodegradable" describes a substance which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 50 weight percents of the substance decompose within a time period shorter than one year.

The term "biodegradable" as used in the context of embodiments of the invention, also encompasses the term "bioresorbable", which describes a substance that decomposes under physiological conditions to break down products that undergo bioresorption into the host-organism, namely, become metabolites of the biochemical systems of the host-organism.

The polymers can be water-soluble or water-insoluble. In some embodiments, the polymers are water soluble at room temperature.

The polymers can further be charged polymers or non-charged polymers. Charged polymers can be cationic polymers, having positively charged groups and a positive net charge at a physiological pH; or anionic polymers, having negatively charged groups and a negative net charge at a physiological pH. Non-charged polymers can have positively charged and negatively charged group with a neutral net charge at physiological pH, or can be non-charged.

In some embodiments, the polymer has an average molecular weight in the range of 100 Da to 800 kDa. In some embodiments, the polymer has an average molecular weight lower than 60 kDa. In some embodiments, the polymer's average molecular weight range is 15 to 40 kDa.

Polymeric substances that have a molecular weight higher than 10 kDa typically exhibit an EPR effect, as described herein, while polymeric substances that have a molecular weight of 100 kDa and higher have relatively long half-lives in plasma and an inefficient renal clearance. Accordingly, a molecular weight of a polymeric conjugate can be determined while considering the half-life in plasma, the renal clearance, and the accumulation in the tumor of the conjugate.

The molecular weight of the polymer can be controlled, at least to some extent, by the degree of polymerization (or co-polymerization).

The polymer used in the context of embodiments of the invention can be a synthetic polymer or a naturally-occurring polymer. In some embodiments, the polymer is a synthetic polymer.

The polymeric backbone of the polymer described herein may be derived from, for example, polyacrylates, polyvinyls, polyamides, polyurethanes, polyimines, polysaccharides, polypeptides, polycarboxylates, and mixtures thereof.

Exemplary polymers which are suitable for use in the context of the present embodiments include, but are not limited to the group consisting of dextran, a water soluble polyamino acid, a polyethylenglycol (PEG), a polyglutamic acid (PGA), a polylactic acid (PLA), a polylactic-co-glycolic acid (PLGA), a poly(D,L-lactide-co-glycolide) (PLA/PLGA), a poly(hydroxyalkylmethaacrylamide), a polyglycerol, a polyamidoamine (PAMAM), and a polyethylenimine (PEI).

These polymers can be of any molecular weight, as described herein.

In some embodiments, the polymeric backbone is derived from a poly(hydroxyalkylmethaacrylamide) or a copolymer thereof. Such a polymeric backbone comprises methacrylamide backbone units having attached thereto either 2-hydroxypropyl groups or such 2-hydroxypropyl groups that have been modified by attaching thereto (directly or indirectly) the moieties described herein (e.g., the bisphosphonate and the anti-angiogenesis agent).

Poly(hydroxyalkylmethacrylamide) (HPMA) polymers are a class of water-soluble synthetic polymeric carriers that have been extensively characterized as biocompatible, non-immunogenic and non-toxic. One advantage of HPMA polymers over other water-soluble polymers is that they may be tailored through relatively simple chemical modifications, in order to regulate their respective drug and targeting moiety content. Further, the molecular weight and charge of these polymers may be manipulated so as to allow renal clearance and excretion from the body, or to alter biodistribution while allowing tumor targeting.

It is to be understood that the polymers as discussed herein describe those polymers that are formed from homogenic or heterogenic, non-functionalized monomeric units, and that the polymeric backbone constituting the polymeric conjugate corresponds to such polymers by being comprised of the same monomeric units, while some of these monomeric units are functionalized, as described herein. Thus, the polymeric backbone of the polymeric conjugate is similar to that of the polymers described herein, and differs from the polymers by having the above-described agents attached to some of the backbone units therein.

In each of the conjugates described herein, the bone targeting moiety and the anti-angiogenesis agent can each be linked to the respective portion of the backbone units in the polymeric backbone directly, or indirectly, through a linker moiety (also referred to herein as a linker, a linker group or a linking group), whereby, in some embodiments, the direct/indirect linkage is designed as being cleavable at conditions characterizing the desired bodily site (e.g., by certain enzymes or pH), as detailed hereinbelow.

Hence, according to some embodiments of the invention, at least one of the anti-angiogenesis agent and the bone targeting moiety is attached to the polymer via a linker. In some embodiments, each of the anti-angiogenesis agent and the bone targeting moiety is attached to the polymer via a linker. The linker linking the anti-angiogenesis agent to the polymer and the linker linking the bone targeting moiety to the polymer may be the same or different.

The linker described herein refers to a chemical moiety that serves to couple the anti-angiogenesis agent and/or the bone targeting moiety to the polymeric backbone while not adversely affecting either the targeting function of the bone targeting moiety or the therapeutic effect of the anti-angiogenesis agent.

In some embodiments, the linker is a biodegradable linker.

The phrase "biodegradable linker", as used herein, describes a linker that is capable of being degraded, or cleaved, when exposed to physiological conditions. Such physiological conditions can be, for example, pH, a certain enzyme, and the like.

In some embodiments, the linker is capable of being cleaved by pre-selected cellular enzymes, for instance, those found in osteoblasts, osteoclasts, lysosomes of cancerous cells or proliferating endothelial cells. Alternatively, an acid hydrolysable linker could comprise an ester or amide linkage and be for instance, a cis-aconityl linkage. Such linkers further enhance the therapeutic activity and reduced toxicity of the conjugates described herein, by allowing the release of the anti-angiogenesis drug and/or the alendronate only at the desired bodily site.

Accordingly, according to some embodiments, the biodegradable linker is a pH-sensitive linker or an enzymatically-cleavable linker.

A pH-sensitive linker comprises a chemical moiety that is cleaved or degraded only when subjected to a certain pH condition, such as acidic pH (e.g., lower than 7), neutral pH (6.5-7) or basic pH (higher than 7).

Such a linker may, for example, be designed to undergo hydrolysis under acidic or basic conditions, and thus, the conjugate remains intact and does not release the agents attached to the polymer in the body, until its reaches a physiological environment where a pH is either acidic or basic, respectively.

Exemplary pH-sensitive linkers include, but are not limited to, a hydrazone bond, ester (including orthoester) bond, amide bond of cis-aconytil residue, a trityl group, acetals, ketals, Gly-ester and a -[Gly-Phe-Gly]- moiety (SEQ ID NO:7).

In some embodiments, the biodegradable linker is an enzymatically-cleavable linker.

Such a linker is typically designed so as to include a chemical moiety, typically, but not exclusively, an amino acid sequence, that is recognized by a pre-selected enzyme. Such an amino acid sequence is often referred to in the art as a "recognition motif". A conjugate comprising such a linker typically remains substantially intact in the absence of the pre-selected enzyme in its environment, and hence does not cleave or degrade so as to the release the agent attached thereto until contacted with the enzyme.

In some embodiments, the enzymatically cleavable linker is cleaved by an enzyme which is expressed in tumor tissues. In some embodiments, the enzymatically cleavable linker is cleaved by an enzyme which is overexpressed in tumor tissues. A conjugate comprising such a linker ensures, for example, that a substantial amount of the conjugated anti-angiogenesis agent is released from the conjugate only at the tumor tissue, thus reducing the side effects associated with non-selective administration of the drug and further enhancing the concentration of the drug at the tumor site.

Exemplary enzymes which are suitable for use in the context of embodiments of the invention include, but are not limited to Cathepsin B, Cathepsin K, Cathepsin D, Cathepsin H, Cathepsin L, legumain, MMP-2 and MMP-9.

Suitable linkers include but are not limited to alkyl chains; alkyl chains optionally substituted with one or more substituents and in which one or more carbon atoms are optionally interrupted by a nitrogen, oxygen and/or sulfur heteroatom.

Other suitable linkers include amino acids and/or oligopeptides.

Such alkyl chains and/or oligopeptides can optionally be functionalized so as allow their covalent binding to the moieties linked thereby (e.g., the polymeric backbone and the bone targeting moiety, the polymeric backbone and the anti-angiogenesis agent). Such a functionalization may include incorporation or generation of reactive groups that participate in such covalent bindings, as detailed hereinunder.

In some embodiment, the linker is a biodegradable oligopeptide group which contains, for example, from 2 to 10 amino acid residues.

In some embodiments the linker is a Cathepsin B-cleavable linker.

Cathepsin B is a lysosomal enzyme overexpressed in both epithelial and endothelial tumor cells. Suitable linkers having cathepsin-B cleavable sites include amino acid sequences such as, but are not limited to, -[Arg]-, -[Cit-Val]- (SEQ ID NO:5), -[Arg-Arg]- (SEQ ID NO:16), -[Phe-Lys]- (SEQ ID NO:10), [Gly-Phe-Leu-Gly] (SEQ ID NO:3), -[Gly-Phe-Ala-Leu]- (SEQ ID NO:17) and -[Ala-Leu-Ala-Leu]-(SEQ ID NO:9), -[Gly-Leu-Gly]- (SEQ ID NO:6), -[Gly-Phe-Gly]- (SEQ ID NO:7), -[Gly-Phe-Leu-Gly-Phe-Lys]- (SEQ ID NO:11) and combinations thereof.

In some embodiments, the linker comprises the amino acid sequences -[Gly-Leu-Gly]- (SEQ ID NO:6), -[Gly-Phe-Gly]- (SEQ ID NO:7), -[Gly-Leu-Phe-Gly]-(SEQ ID NO:8), -[Gly-Phe-Leu-Gly]- (SEQ ID NO:3), -[Phe-Lys]- (SEQ ID NO:10), and/or -[Gly-Phe-Leu-Gly-Phe-Lys]- (SEQ ID NO:11).

In some embodiments, the linker is -[Gly-Phe-Leu-Gly-Phe-Lys]- SEQ ID NO:11). Such a linker comprises two "recognition motifs" of Cathepsin B, and a cleavage thereof so as to release the moiety attached thereto is effected only in the presence of high enzyme concentration. This feature enhances the selective release of the attached moiety at a site where the enzyme is overexpressed.

In some embodiments, the linker is -[Gly-Phe-Leu-Gly]- (SEQ ID NO:3).

As demonstrated in the examples section herein below, the Cathepsin B cleavable linkers being -[Gly-Phe-Leu-Gly-Phe-Lys]- (SEQ ID NO:11) and -[Gly-Phe-Leu-Gly]- (SEQ ID NO:3) were used, linking Paclitaxel and Alendronate to HPMA (see, FIG. 1). The -[Gly-Phe-Leu-Gly-Phe-Lys]- hexapeptide (SEQ ID NO: 11) is not directly attached to the Paclitaxel drug but rather a p-aminobenzyl carbonate (PABC) spacer, as detailed hereinbelow. Shown in FIG. 1 is a schematic representation of the Cathepsin B cleavage of the conjugate whereby Cathepsin B cleaves the HPMA copolymer-paclitaxel-FK-ALN conjugate (SEQ ID NO: 12) at (1) the two amide bonds of the paxlitaxel-hexapeptide linker (between Gly-Phe-Leu-Gly (SEQ ID NO: 3) and the Phe-Lys (SEQ ID NO:10) amino acids, and between the Phe-Lys (SEQ ID NO: 10) and the PABC) and (2) the amide bond of the ALN tetrapeptide linker (the Gly-Phe-Leu-Gly). The products of the cathepsin B cleavage are PABC-Paclitaxel and ALN. Free Paclitaxel, the final product, is obtained from PABC-Paclitaxel through spontaneous 1,6-benzyl elimination, as discussed in detail hereinbelow. It is to be understood that the polymeric conjugate referred to herein as HPMA copolymer-paclitaxel-FK-ALN conjugate (SEQ ID NO: 12) comprises a polymeric backbone derived from HPMA monomeric units, to which both Paclitaxel and alendronate are attached via a Cathepsin B-biodegradable linker, whereby the Paclitaxel is attached to the polymeric backbone via a linker that comprises -[Phe-Lys]- (denoted as FK, SEQ ID NO:10).

The release of Paclitaxel from the conjugate via a Cathepsin B-dependent mechanism has been demonstrated in the Examples section that follows. Specifically, the HPMA copolymer-Paclitaxel-FK-ALN conjugate (SEQ ID NO: 12) was incubated with Cathepsin B and the extent of Paclitaxel release from the conjugate increased in correlation with the cathepsin B incubation time (FIG. 4). Furthermore, the anti-proliferative activity of Paclitaxel against HUVEC was reduced significantly when the Paclitaxel was conjugated to the HPMA copolymer via a linker sequence unrecognized by Cathepsin B (GGGG, SEQ ID NO:18) as compared to a corresponding conjugate having a linker which is cleaved by cathepsin B (GGFK; SEQ ID NO:19, see FIG. 6). The involvement of Cathepsin B in the release of Paclitaxel from the conjugate was further demonstrated by the reduced anti-proliferative activity of the conjugate when a Cathepsin B inhibitor was added (FIG. 7).

In some embodiments the enzymatically cleavable linker is cleaved by Cathepsin K.

Cathepsin K is a lysosomal cysteine protease involved in bone remodeling and resorption and is predominantly expressed in osteoclasts. Its expression is stimulated by inflammatory cytokines that are released after tissue injury and in bone neoplasms [Pan et al. 2006, *J Drug Target* 14:425-435; Husmann et al. 2008, *Mol Carcinog* 47: 66-73].

A non-limiting example of a linker having Cathepsin K cleavable sites is -[Gly-Gly-Pro-Nle]- (SEQ ID NO:20).

An oligopeptide linker which contains the pre-selected amino acid sequence (recognition motif) can also be constructed such that the recognition motif is repeated several times within the linker, to thereby enhance the selective release of the attached agent. Various recognition motifs of the same or different enzymes can also be incorporated within the linker. Similarly, the linker may comprise multiple pH sensitive bonds or moieties. Linkers comprising such multiple cleavable sites can enhance the selective release of the anti-angiogenesis agent at the desired bodily site, thereby reducing adverse side effects, and further enhance the relative concentration of the released drug at the bodily site when it exhibits its activity.

In cases where the anti-angiogenesis agent and/or the bone targeting moiety is bound directly to the polymer, the bond linking these moieties can also be biodegradable, for example, an enzymatically-cleavable bond or a pH-sensitive bond. Such a bond can be formed upon functionalizing the polymer, the bone targeting moiety and/or the anti-angiogenesis agent, so as to include compatible reactive groups for forming the required bond.

The peptide linker may also include a peptide sequence which serves to increase the length of the linker. Longer peptides may be advantageous due to a more efficient steric interaction of the linker with the cleaving enzyme.

In some embodiments the anti-angiogenesis agent is linked to the polymeric backbone or to the linker via a spacer. In some embodiments the bone targeting moiety is linked to the polymeric backbone or to the linker via a spacer. The spacers can be the same or different.

The term "spacer" as used herein describes a chemical moiety that is covalently attached to, and interposed between, the polymeric backbone and the linker, the anti-angiogenesis agent and/or the bone targeting moiety, thereby forming a bridge-like structure between the polymeric backbone and the anti-angiogenesis agent and/or the bone targeting moiety. Alternatively, the spacer may be covalently attached to, and interposed between, the linker and the anti-angiogenesis agent and/or the bone targeting moiety.

Suitable spacers include, but are not limited to, alkylene chains, optionally substituted by one or more substituents and which are optionally interrupted by one or more nitrogen, oxygen and/or sulfur heteroatom.

Other suitable spacers include amino acids and amino acid sequences, optionally functionalized with one or more reactive groups for being coupled to the polymeric backbone/anti-angiogenesis agent/bone targeting moiety/linkers.

In some embodiments, the spacer has the formula G-$(CH_2)_n$-K, wherein n is an integer from 1 to 10; and G and K are each a reactive group such as, for example, NH, O or S. In some embodiments, G and K are each NH and n is 2.

In some embodiments, the spacer is an amino acid sequence, optionally an inert amino acid sequence (namely, does not affect the affinity or selectivity of the conjugate). Such a spacer can be utilized for elongating or functionalizing the linker.

In some cases, a spacer is utilized for enabling a more efficient and simpler attachment of the bone targeting moiety and/or the anti-angiogenesis agent to the polymeric backbone or linker, in terms of steric considerations (renders the site of the polymer to which coupling is effected less hindered) or chemical reactivity considerations (adds a compatible reactive group to the site of the polymer to which coupling is effected). In some cases, the spacer may contribute to the performance of the resulting conjugate. For example, the spacer may render an enzymatically cleavable spacer less sterically hindered and hence more susceptible to enzymatic interactions.

In some cases the spacer is utilized for enabling a more efficient and simpler synthesis of the conjugate by, for example, altering the solubility of the anti-angiogenesis agent and/or the bone targeting moieties to which the spacer is attached (i.e. either more hydrophobic or more hydrophilic).

In some embodiments, the spacer is a degradable spacer, which is capable of undergoing degradation reactions so as to release the agent attached thereto. In some embodiments, the spacer is biodegradable, as defined herein.

The spacer can be, for example, a substituted or unsubstituted cycloalkyl group, a substituted or unsubstituted heteroalicyclic group, a substituted or unsubstituted aryl group and a substituted or unsubstituted heteroaryl group; wherein the substituents can be, for example, hydroxy, alkoxy, thiohydroxy, thioalkoxy, cyano, nitro, carbonyl, thiocarbonyl, C-carboxy, O-carboxy, O-carbamyl, N-carbamyl, O-thiocarbamyl, N-thiocarbamyl, sulfinyl, sulfonyl, C-amido, N-amido, amino and NRaRb wherein Ra and Rb are each independently hydrogen, alkyl, cycloalkyl, aryl, carbonyl, sulfonyl, trihalomethysulfonyl and, when combined, a five- or six-member heteroalicyclic ring, whereby the spacer may be linked to the anti-angiogenesis agent/bone targeting moiety/linker/polymer either directly, through the cyclic group or alternatively, via one or more of the substituents.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it means that the group, in this case the alkyl group, may contain 1 carbon atom, 2 carbon atoms, 3 carbon atoms, etc., up to and including 20 carbon atoms. In some embodiments, the alkyl group has 1-10 carbon atoms. In some embodiments, the alkyl group has 1-4 carbon atoms. Exemplary alkyl groups include, but are not limited to methyl, ethyl, propyl, butyl, pentyl, hexyl, heptyl, octyl, nonyl, decyl, undecyl, dodecyl, tridecyl, tetradecyl, pentadecyl, heptadecyl, octadecyl and nonadecyl.

The term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane.

The term "aryl" describes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system.

The term "hydroxy" describes an —OH group.

The term "alkoxy" describes both an —O-alkyl and an —O-cycloalkyl group, as defined herein.

The term "thiol" describes a —SH group.

The term "thioalkoxy" describes both an —S-alkyl group, and an —S-cycloalkyl group, as defined herein.

The term "cyano" describes a —C≡N group.

The term "carbonyl" describes a —C(=O)—R' group, where R' is hydrogen, alkyl, cycloalkyl, aryl, heteroaryl (bonded through a ring carbon) or heteroalicyclic (bonded through a ring carbon) as defined herein.

The term "thiocarbonyl" describes a —C(=S)—R' group, where R' is as defined herein.

The term "O-carbamyl" describes an —OC(=O)—NR'R" group, where R' is as defined herein and R" is hydrogen, alkyl, cycloalkyl, aryl, heteroaryl (bonded through a ring carbon) or heteroalicyclic (bonded through a ring carbon) as defined herein.

The term "N-carbamyl" describes an R'OC(=O)—NR"— group, where R' and R" are as defined herein.

The term "O-thiocarbamyl" describes an —OC(=S)—NR'R" group, where R' and R" are as defined herein.

The term "N-thiocarbamyl" describes an R"OC(=S)NR'— group, where R' and R" are as defined herein.

The term "C-amido" describes a —C(=O)—NR'R" group, where R' and R" are as defined herein.

The term "N-amido" describes an R'C(=O)—NR" group, where R' and R" are as defined herein.

The term "C-carboxy" describes a —C(=O)—O—R' groups, where R' is as defined herein.

The term "O-carboxy" describes an R'C(=O)—O— group, where R' is as defined herein.

The term "nitro" group describes an —NO$_2$ group.

The term "amino" group describes an —NH$_2$ group.

The term "sulfonyl" group describes an —S(=O)$_2$—R' group, where R' is as defined herein.

The term "halogen" or "halo" describes fluoro, chloro, bromo or iodo atom.

In some embodiments the spacer is a substituted or unsubstituted aryl group and substituted or unsubstituted heteroaryl group whereby the substituents can be carbonate, C-amido, N-amido and amine, whereby the spacer may be linked to the anti-angiogenesis agent/bone targeting moiety/linker/polymer either directly, through the aromatic group or alternatively, via one or more of the substituents.

In some embodiments, the spacer is a degradable spacer selected such that it undergoes a spontaneous degradation once it is cleaved from the polymeric conjugate.

Such a spacer can be, for example, attached to a biodegradable linker at one end and to an anti-angiogenesis agent or a bone targeting moiety at another end, such that once the biodegradable linker is cleaved, so as to release the spacer and the moiety attached thereto, the spacer undergoes a spontaneous degradation so as to release the moiety attached thereto.

Exemplary spacers that can undergo such a spontaneous degradation include, but are not limited, chemical moieties that can undergo a spontaneous 1,4-, 1,6-, 1,8-, etc. elimination, via a cascade of immolative electronic reactions. Such chemical groups are known in the art, or, otherwise, can be devised by those skilled in the art.

In an exemplary embodiment, the spacer is such that can undergo a spontaneous 1,6-benzyl elimination. An example of such a spacer is p-aminobenzyl carbonate (PABC).

In some embodiments, the spacer facilitates the attachment of the anti-angiogenesis agent or the bone targeting moiety to the polymeric backbone or the linker. This may be effected by imparting a reactive group to the moiety to be attached, which is chemically compatible with functional groups in the polymeric backbone and/or the linker attached to the polymeric backbone, and/or by modifying the solubility of the moiety to be attached to the polymer, so as to facilitate the reaction between the polymer (or co-polymer) and the moiety.

For example, in some cases the polymer constituted by the polymeric backbone is a water-soluble polymer while the anti-angiogenesis agent is hydrophobic, and hence has a limited solubility in aqueous solutions or in polar organic solvents. In such cases, a spacer can be attached to the anti-angiogenesis agent so as to enhance the water solubility thereof and to facilitate the conjugation thereof to the polymer in an aqueous solution or a protic or polar organic solvent.

As discussed hereinabove, a spacer being a p-aminobenzyl carbonate (PABC) has been used by the present inventors to link Paclitaxel through a -[Gly-Phe-Leu-Gly-Phe-Lys]-(SEQ ID NO:11) linker to the HPMA polymer (see, FIG. 1).

As further discussed, upon cleavage of the conjugate by cathepsin B, PABC-Paclitaxel is released and free Paclitaxel, the final product, is obtained from PABC-Paclitaxel through spontaneous 1,6-benzyl elimination.

Such a PABC spacer therefore serves for both (i) facilitating the attachment of paclitaxel to a linker; and (ii) allowing a spontaneous release of paclitaxel upon biodegradation of the linker, followed by degradation of the spacer.

A spacer may also be used in order to attach other agents (e.g., a labeling agent, as described hereinbelow) to the conjugate.

The spacer may be varied in length and in composition, depending on steric consideration and may be used to space the anti-angiogenesis agent and/or bone targeting moiety form the polymeric backbone.

In some embodiments the conjugate described herein is such that the anti-angiogenesis agent is Paclitaxel, which linked through a linker being -[Gly-Phe-Leu-Gly-Phe-Lys]- (SEQ ID NO:11) to a HPMA-derived polymeric backbone, and the bone targeting moiety in linked to the polymeric backbone via a -[Gly-Phe-Leu-Gly]- linker (SEQ ID NO:3). In some embodiments, the bone targeting moiety is alendronate.

Herein, the phrases "loading onto the polymer", or simply "load", are used to describe the amount of an agent that is attached to the polymeric backbone of the conjugates described herein, and is represented herein by the mol % of this agent in the conjugate, as defined hereinafter.

As used herein, the term "mol %" describes the number of moles of an attached moiety per 1 mol of the polymeric conjugate, multiplied by 100.

Thus, for example, a 1 mol % load of an bone targeting moiety describes a polymeric conjugate composed of 100 backbone units, whereby 1 backbone unit has a targeting moiety attached thereto and the other 99 backbone units are either free or have other agents attached thereto.

The optimal degree of loading of the anti-angiogenesis agent and bone targeting moiety for a given conjugate and a given use is determined empirically based on the desired properties of the conjugate (e.g., water solubility, therapeutic efficacy, pharmacokinetic properties, toxicity and dosage requirements), and optionally on the amount of the conjugated moiety that can be attached to a polymeric backbone in a synthetic pathway of choice.

The % loading can be measured by methods well known by those skilled in the art, some of which are described hereinbelow under the Materials and Methods of the Examples section that follows.

In some embodiments, the loading of the anti-angiogenesis agent in the polymer is greater than 1 mol %.

In some embodiments, the loading of the anti-angiogenesis agent in the conjugate ranges from 1 mol % to 99 mol %, from 1 mol % to 50 mol %, from 1 mol % to 20 mol %, from 1 mol % to 10 mol %, or from 1 mol % to 5 mol %.

In some embodiments, the loading of the bone targeting moiety is greater than 1 mol %.

In some embodiments, the loading of the bone targeting moiety in the conjugate ranges from 1 mol % to 99 mol %, from 1 mol % to 50 mol %, from 1 mol % to 20 mol %, from 1 mol % to 10 mol %, or from 1 mol % to 5 mol %.

The number of backbone units within the polymeric backbone that have an anti-angiogenesis agent conjugated thereto is defined herein as "y", the number of backbone units within the polymeric backbone that have a bone targeting moiety conjugated thereto is herein defined as "w" and the number of free backbone units in the polymeric backbone (which are not bound to an additional moiety) is herein defined as "x".

Accordingly, in some embodiments, the conjugate described herein can be represented by the general formula I:

$$[A_1]x[A_2\text{-}L_1\text{-}B]y[A_3\text{-}L_2\text{-}D]w \qquad \text{Formula I}$$

wherein:

x is an integer having a value such that $x/(x+y+w)$ multiplied by 100 is in the range of from 0.01 to 99.9;

y is an integer having a value such that $y/(x+y+w)$ multiplied by 100 is in the range of from 0.01 to 99.9; and w is an integer having a value such that $w/(x+y+w)$ multiplied by 100 is in the range of from 0.01 to 99.9, $A_1$, $A_2$ and $A_3$ are each backbone units covalently linked to one another and forming the polymeric backbone, wherein:

B is the anti-angiogenesis agent as defined hereinabove;

D is the bone targeting moiety as defined hereinabove; and each of the $L_1$ and $L_2$ is independently a linker as defined hereinabove;

such that $[A_2\text{-}L_1\text{-}B]$ is a backbone unit having attached thereto the anti-angiogenesis agent; and $[A_2\text{-}L_2\text{-}D]$ is a backbone unit having attached thereto the bone targeting moiety;

wherein each of the $[A_1]$, the $[A_2\text{-}L_1\text{-}B]$ and the $[A_3\text{-}L_2\text{-}D]$ is either a terminal backbone unit being linked to one of the $[A_1]$, the $[A_2\text{-}L_1\text{-}B]$ and the $[A_3\text{-}L_2\text{-}D]$, or is linked to at least two of the $[A_1]$, the $[A_2\text{-}L_1\text{-}B]$ and the $[A_3\text{-}L_2\text{-}D]$ and the $A_1$, $A_2$ and/or $A_3$ are linked to one another to thereby form the polymeric backbone.

In embodiments where the polymeric backbone in the conjugate is derived from HPMA, $A_1$ is a hydroxypropylmethacrylamide unit; and $A_2$ and $A_3$ are each a methacrylamide unit.

In some embodiments, the conjugate described herein can be represented by the general formula II:

Formula II

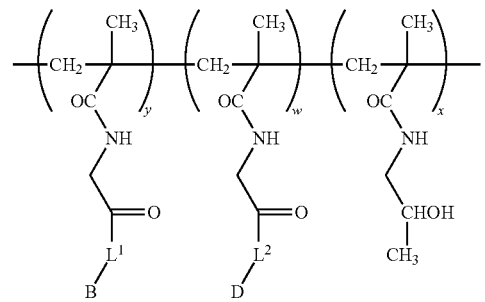

wherein y, w and x are as defined herein.

In some embodiments the conjugate has the structure:

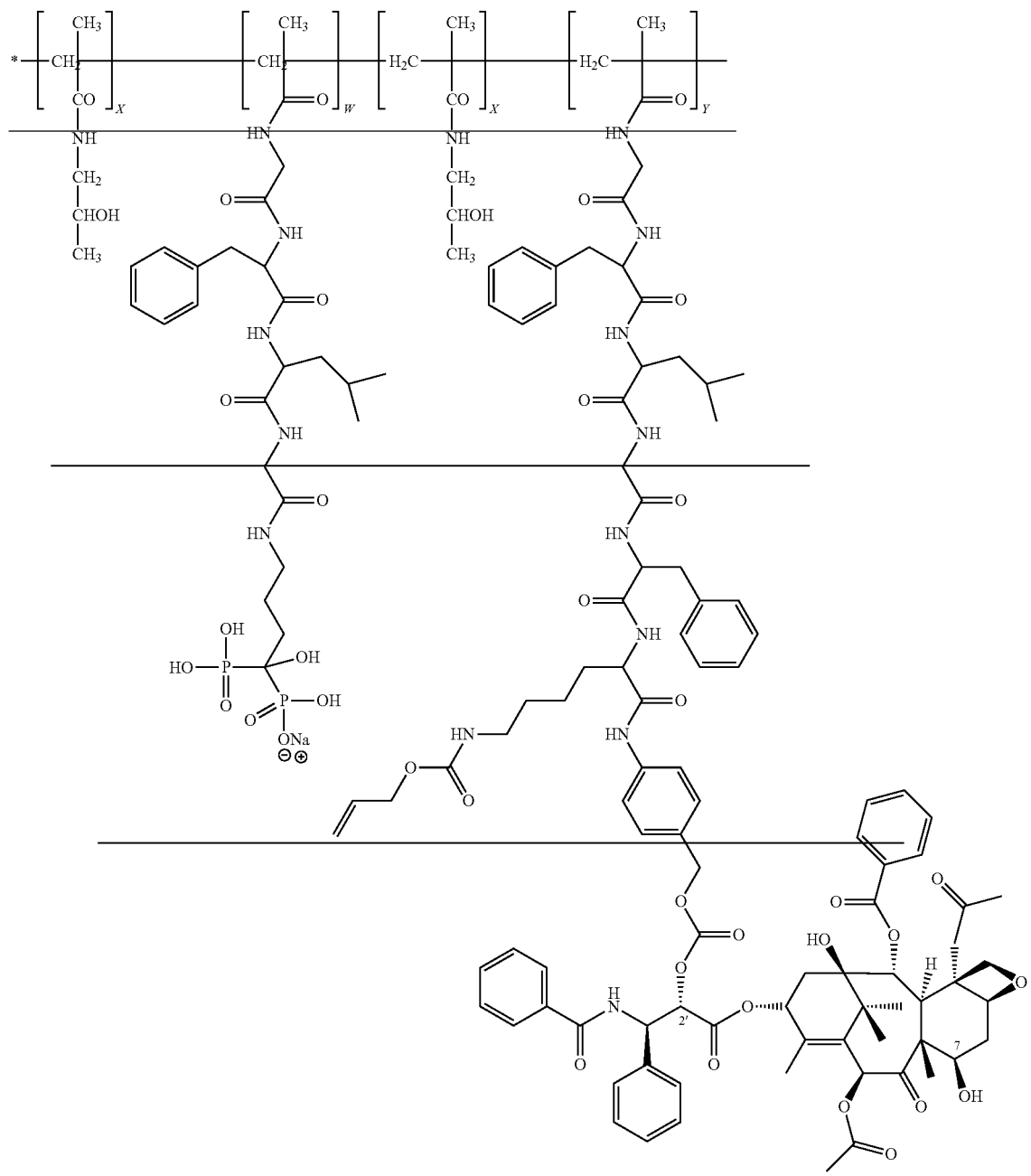

wherein y, w and x are as defined herein.

According to some embodiments of the invention, x is an integer having a value such that x/(x+y+w) multiplied by 100 is in the range of from 70 to 99.9; y is an integer having a value such that y/(x+y+w) multiplied by 100 is in the range of from 0.01 to 15; and w is an integer having a value such that w/(x+y+w) multiplied by 100 is in the range of from 0.01 to 15.

For example x/(x+y+w) multiplied by 100 may be 71, 72, 73, 74, 75, 76, 77, 78, 79, 80, 81, 82, 83, 84, 85, 86, 87, 88, 89, 90, 91, 92, 93, 94, 95, 96, 97, 98, 99 or 99.9; y/(x+y+w) multiplied by 100 may be 0.01, 0.02, 0.03, 0.04, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14 or 15; and w/(x+y+w) multiplied by 100 may be 0.01, 0.02, 0.03, 0.04, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14 or 15.

It would be appreciated that x, y and w can be controlled as desired by selecting the mol ratio of the respective monomeric units used for forming the polymeric conjugate, as discussed hereinbelow.

According to some embodiments, the conjugate described herein further comprises a labeling agent attached thereto.

The attachment of a labeling agent to the conjugate, enables utilizing these conjugates for monitoring bone related disease or disorders, for example, monitoring the therapeutic effect exhibited by the conjugate described herein.

As used herein, the phrase "labeling agent" describes a detectable moiety or a probe. Exemplary labeling agents which are suitable for use in the context of these embodiments include, but are not limited to, a fluorescent agent, a radioactive agent, a magnetic agent, a chromophore, a bioluminescent agent, a chemiluminescent agent, a phosphorescent agent and a heavy metal cluster.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}Tc$, $^{18}F$, $^{131}I$ and $^{125}I$.

The term "magnetic agent" describes a substance which is attracted to an externally applied magnetic field. These substances are commonly used as contrast media in order to improve the visibility of internal body structures in Magnetic resonance imaging (MRI). The most commonly used compounds for contrast enhancement are gadolinium-based. MRI contrast agents alter the relaxation times of tissues and body cavities where they are present, which depending on the image weighting can give a higher or lower signal.

As used herein, the term "chromophore" describes a chemical moiety that, when attached to another molecule, renders the latter colored and thus visible when various spectrophotometric measurements are applied.

The term "bioluminescent agent" describes a substance which emits light by a biochemical process.

The term "chemiluminescent agent" describes a substance which emits light as the result of a chemical reaction.

The phrase "fluorescent agent" refers to a compound that emits light at a specific wavelength during exposure to radiation from an external source.

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques.

As discussed hereinabove, the tumor vasculature possesses an enhanced capacity for the uptake of macromolecules and colloidal drug carriers having a high molecular weight and large hydrodynamic diameter due to the EPR effect. Therefore, a conjugate as described herein, having a large enough hydrodynamic diameter is beneficial. The term "large enough" is used herein to describe a conjugate having a hydrodynamic diameter which leads to an increase in the ratio of conjugate accumulated in the tumor tissue as compared to other tissues. The determination of the optimal ratio is well within the capability of those skilled in the art. For example, the ratio may be 1.1, 2, 3, 4, 5 etc. In some embodiments, the hydrodynamic diameter is in the range of from 15 nm to 200 nm. In some embodiments, the hydrodynamic diameter is in the range of from 50 nm to 150 nm. In some embodiments the hydrodynamic diameter is in the range of from 70 nm to 90 nm. In yet another embodiment the hydrodynamic diameter is 95 nm. The hydrodynamic diameter can be measured as described below under the Materials and Methods of the Example section which follows hereinbelow.

The conjugates described hereinabove may be administered or otherwise utilized in this and other aspects of the present invention, either as is, or as a pharmaceutically acceptable salt, enantiomer, diastereomer, solvate, hydrate or a prodrug thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds are preferably regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention.

The phrase "pharmaceutically acceptable salts" is meant to encompass salts of the moieties and/or conjugates which are prepared with relatively nontoxic acids or bases, depending on the particular substituents found on the compounds described herein. When conjugates of the present invention contain relatively acidic functionalities, base addition salts can be obtained by contacting the neutral (i.e., non-ionized) form of such conjugates with a sufficient amount of the desired base, either neat or in a suitable inert solvent. Examples of pharmaceutically acceptable base addition salts include sodium, potassium, calcium, ammonium, organic amino, or magnesium salt, or a similar salt. When conjugates of the present invention contain relatively basic functionalities, acid addition salts can be obtained by contacting the neutral form of such conjugates with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific conjugates of the present invention contain both basic and acidic functionalities that allow the conjugates to be converted into either base or acid addition salts.

The neutral forms of the conjugates are preferably regenerated by contacting the salt with a base or acid and isolating the parent conjugate in a conventional manner. The parent form of the conjugate differs from the various salt forms in certain physical properties, such as solubility in polar solvents, but otherwise the salts are equivalent to the parent form of the conjugate for the purposes of the present invention.

In an example, a pharmaceutically acceptable salt of alendronate is utilized. An exemplary such salt is sodium alendronate. An alendronate-containing conjugate can therefore comprise a sodium salt of alendronate.

The term "prodrug" refers to an agent, which is converted into the active compound (the active parent drug) in vivo. Prodrugs are typically useful for facilitating the administration of the parent drug. The prodrug may also have improved solubility as compared with the parent drug in pharmaceutical compositions. Prodrugs are also often used to achieve a sustained release of the active compound in vivo.

The conjugates described herein may possess asymmetric carbon atoms (optical centers) or double bonds; the racemates, diastereomers, geometric isomers and individual isomers are encompassed within the scope of the present invention.

As used herein, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The conjugates described herein can exist in unsolvated forms as well as solvated forms, including hydrated forms. In general, the solvated forms are equivalent to unsolvated forms and are encompassed within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

Certain conjugates of the present invention may exist in multiple crystalline or amorphous forms. In general, all physical forms are equivalent for the uses contemplated by the present invention and are intended to be within the scope of the present invention.

While reducing the present invention to practice, the present inventors have designed and successfully practiced novel processes for preparing a HPMA co-polymer having attached thereto an anti-angiogenesis agent, a bone targeting moiety and optionally a labeling agent. It is noted that synthesizing such a polymeric conjugate is subjected to various limitations, imposed by a different solubility of the moieties to be conjugates, complicated desired structural features that are required for optimal performance of the conjugate, incompatibility of the reactants, and the like. Hence, devising a process that overcomes these limitations and is designed to obtain a conjugate that exhibits at least a reasonable performance is highly advantageous.

Hence, according to another aspect of embodiments of the invention there is provided a process of synthesizing the conjugate described herein, the process comprising:

(a) co-polymerizing a plurality of monomeric units which form the polymeric backbone, wherein a portion of the plurality of the monomeric units comprises monomeric units terminating by a first reactive group, and another portion of the plurality comprises monomeric units terminating by a second reactive group, to thereby obtain a co-polymer comprising a polymeric backbone that comprises a plurality of backbone units, wherein a portion of the backbone units has the first reactive group and another portion of the backbone units has the second reactive group, the first reactive group being capable of reacting with the anti-angiogenesis agent and the second reactive being capable of reacting with the bisphosphonate;

(b) reacting the co-polymer with the anti-angiogenesis agent or with a derivative thereof, via the first reactive group, to thereby obtain the co-polymer having said anti-angiogenesis agent attached thereto; and (c) reacting the co-polymer with the bisphosphonate or a derivative thereof, via said second reactive group, to thereby obtain the co-polymer having the bisphosphonate attached thereto, thereby obtaining the conjugate.

Reacting the co-polymer with an anti-angiogenesis agent (b) can be performed subsequent to, concomitant with or prior to reacting the co-polymer with the bisphosphonate bone targeting moiety (c).

The monomeric units described herein, which terminate by a reactive group, are also referred to herein as functionalized monomers or functionalized monomeric units.

The co-polymer formed by the co-polymerization is also referred to herein as a functionalized co-polymer.

In some embodiments, the co-polymerization can be effected in the presence of monomeric units which form the polymeric backbone, and which are non-functionalized.

As used herein, a "reactive group" describes a chemical group that is capable of reacting with another group so as to form a chemical bond, typically a covalent bond. Optionally, an ionic or coordinative bond is formed.

A reactive group is termed as such if being chemically compatible with a reactive group of an agent or moiety that should be desirably attached thereto. For example, a carboxylic group is a reactive group suitable for conjugating an agent or a moiety that terminates with an amine group, and vice versa.

A reactive group can be inherently present in the monomeric units forming the backbone units, or be generated therewithin by terms of chemical modifications of the chemical groups thereon or by means of attaching to these chemical groups a spacer or a linker that terminates with the desired reactive group.

Generally, the anti-angiogenesis agent or bone targeting moiety can be attached to the monomeric units that form the polymeric backbone, or to the backbone units of the copolymer, by means of a functional group that is already present in the native molecule and/or the backbone units of the polymer, or otherwise can be introduced by well-known procedures in synthetic organic chemistry without altering the activity of the agent.

For example, the bone targeting moiety and the anti-angiogenesis agent can be attached to the polymeric backbone via an amide bond between the terminal carboxylic group of a peptidic linker and an amine group located in the bone targeting moiety and/or the anti-angiogenesis. Alternatively, as demonstrated in the Examples section that follows, the addition of a functional group being p-nitrophenol group (—ONp) to the polymer being HPMA copolymer which already comprises the peptidic linker Gly-Phe-Leu-Gly-ONp (i.e. HPMA-Gly-Phe-Leu-Gly-ONp; SEQ ID NO:21) activated the last amino acid of the linker (Gly) thus enabling a more efficient and easier attachment of the bone targeting moiety being alendronate and the anti-angiogenesis agent being Paclitaxel, to the polymer via the formation of an amide bond with the glycine (see, FIG. 2). In some embodiments, the bone targeting moiety and/or the anti-angiogenesis moiety are modified prior to being conjugated to the functionalized polymer, so as to include reactive groups that are compatible with the first and second reactive groups, respectively, of the functionalized co-polymer.

Such a modification can be effected by means of attaching a spacer and/or a linker to the bone targeting moiety and/or the anti-angiogenesis agent prior to the conjugation thereof to the functionalized co-polymer.

Hence, in some embodiments, the process is further effected by preparing such modified bone targeting moiety and/or anti-angiogenesis agent.

The linkers and/or spacers interposed between the polymeric backbone and the moieties conjugated thereto are designed so as to exhibit the properties described elaborately hereinabove with respect thereto.

The copolymerization of the various monomeric units can be effected by any polymerization method known in the art, using suitable polymerization initiators and optionally chain transfer agents. Such suitable polymerization initiators and chain transfer agents can be readily identified by a person skilled in the art.

As demonstrated in the Examples section that follows, the copolymerization can be performed via two methodologies: the "classical" methodology, being a thermopolymerization, and the "reversible addition-fragmentation chain transfer" (RAFT) polymerization technique.

Using the RAFT approach enables to perform the copolymerization at room temperature.

The "reversible addition-fragmentation chain transfer" (RAFT) polymerization technique typically involves the use of thiocarbonylthio compounds, such as dithioesters, dithiocarbamates, trithiocarbonates, and xanthates in order to mediate the polymerization via a reversible chain-transfer process. This allows access to polymers with low polydispersity and high functionality.

In some embodiments, the reactive groups can be protected prior to the respective conjugation thereto. In such cases, the process further comprises deprotecting the reactive group prior to the respective conjugation.

This allows a regio-controlled conjugation of, for example, the anti-angiogenesis agent to those backbone units that comprises a biodegradable linker.

A discussed hereinabove, the conjugates described herein are designed so as to release the anti-angiogenesis agent in the desired bodily site (i.e. sites of bone related disease or disorders). Thus, the anti-angiogenesis agent and/or the bone targeting moiety may be linked to the polymer via a direct linkage or via an indirect linkage, through a linker group, whereby, in some embodiments, the direct/indirect linkage is designed as being cleavable at conditions characterizing the desired bodily site (e.g., by certain enzymes or pH).

Hence, in some embodiments, the monomeric units terminating by the first reactive group and/or the monomeric units terminating by the second reactive group further comprise a linker which terminates by the first reactive group or by the second reactive group.

Accordingly, in some embodiments, the process further comprises, prior to (a), attaching the linker to the respective portion of the monomeric units.

In some embodiments, the linker may be constructed by attaching a first portion of the linker to the polymer and a second portion of the linker to the anti-angiogenesis agent/ bone targeting moiety whereby, upon linking the anti-angiogenesis agent/bone targeting moiety to the polymer the two portion are attached one to the other thus forming the linker.

In some embodiments, the linker is first attached to the anti-angiogenesis agent/bone targeting moiety, followed by the attachment of the linker to the polymer.

In some embodiments, the process further comprises attaching of a spacer, as described herein, to the backbone units of the functionalized copolymer and thereafter coupling to anti-angiogenesis agent and/or the bone targeting moiety to the spacer. Alternatively, the spacer may be attached first to the anti-angiogenesis agent and/or bone targeting moiety, prior to conjugation to the polymeric backbone.

Hence, in some embodiments, in the case that at least one of the anti-angiogenesis agent and the bisphosphonate is linked to the polymeric backbone and/or to the linker via a spacer, the process described herein further comprises, prior to (a), attaching the spacer to at least one of the portions of the monomeric units.

It should be appreciated that the spacers and linkers utilized for coupling the anti-angiogenesis agent and/or the bone targeting moiety to the polymer are designed so as to allow a smooth and efficient conjugation of the respective moiety and an optimal performance of the obtained conjugate, as discussed elaborately hereinabove.

In the case of the polymer and/or the anti-angiogenesis agent and/or bone targeting moiety further comprise a linker, the process is affected by attaching the spacer to the linker moiety.

In some embodiments, the process described herein further comprises, prior to (a), attaching the spacer to the anti-angiogenesis agent and/or to the bisphosphonate, to thereby obtain the derivative of the anti-angiogenesis agent and/or of the bisphosphonate.

In some embodiments the process further comprises attaching a labeling agent, as defined herein, to the formed conjugate. The labeling agent can be attached to either of functionalized monomeric units, prior to co-polymerization or to the formed co-polymer.

In some embodiments, the labeling agent is attached to the co-polymer concomitantly with the bone targeting moiety. Alternatively, it is attached prior to or subsequent to attaching the bone targeting moiety and/or the anti-angiogenesis agent.

Each of the conjugates described in any of the embodiments of the invention, may further include an additional moiety conjugated thereto. Such an additional moiety can be conjugated either to monomeric units within and throughout the polymeric backbone, or be attached at one or both end of the polymeric backbone.

Such an additional moiety can be a labeling agent, as described herein, or an additional targeting moiety or an additional therapeutically active agent, which may improve the performance of the formed conjugate.

As discussed hereinabove, the conjugates described herein comprise a bone targeting moiety which enables the targeting of the conjugate to bone and bone related (osteoid) structures. Due to the anti-angiogenesis/anti-proliferative activity of the conjugate they can be used for treating bone and bone related disease and disorders.

Hence, according to another aspect of some embodiments of the present invention there are provided methods of treating a bone related disease or disorder in a subject in need thereof. These methods are effected by administering to the subject a therapeutically effective amount of any of the conjugates described herein.

Accordingly, according to another aspect of some embodiments of the present invention there are provided uses of any of the conjugates described herein as a medicament. In some embodiments, the medicament is for treating a bone-related disease or disorder.

According to another aspect of some embodiments of the present invention, the conjugates described herein are identified for use in the treatment of a bone related disease or disorder.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The phrase a "bone related disease or disorder" describes a disease or disorder wherein bone formation, deposition, or resorption is abnormal, especially those characterized by excessive angiogenesis. The phrase "bone related disease or disorder" encompasses disease and disorders occurring in bodily sites other than bone which evolved from a bone related disease or disorder such as, for example, metastasis of bone cancer in another organ. Bone-related disorders include, but are not limited to, bone cancer and bone cancer metastases, osteopenia due to bone metastases, periodontal disease, periarticular erosions in rheumatoid arthritis, Paget's disease, malignant hypercalcemia, osteolytic lesions produced by bone metastasis, bone abnormalities caused by cancer therapeutics and hyperostosis.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. When the treatable disease is bone cancer, the term would encompass any inhibition of tumor growth or metastasis, or any attempt to inhibit, slow or abrogate tumor growth or metastasis.

It is noted herein that by targeting an anti-angiogenesis agent via the methodologies described herein, the toxicity of the anti-angiogenesis agent is substantially reduced, due to the conjugate selectivity towards bone tissues. Consequently, besides the use of the conjugates described herein in a clinically evident disease, optionally in combination with other drugs, these conjugates may potentially be used as a long term-prophylactic for individuals who are at risk for relapse due to residual dormant cancers. The use of non-toxic targeted conjugates for the treatment of asymptomatic individuals who are at risk for relapse of osteosarcoma, as an example, may lead to a major paradigm shift in cancer treatment from current methods where treatment is generally not initiated until a bone related disease such as osteosarcoma becomes clinically evident.

The term "subject" (alternatively referred to herein as "patient") as used herein refers to an animal, preferably a mammal, most preferably a human, who has been the object of treatment, observation or experiment.

As demonstrated in the Examples section that follows, an exemplary conjugate, according to some embodiments described herein, being a HPMA copolymer of Paclitaxel and alendronate (HPMA copolymer-PTX-FK-ALN conjugate; SEQ ID NO:12) inhibited angiogenesis as well as cell proliferation and therefore can be utilized for the treatment of bone related disease and disorders characterized by pathologically excessive angiogenesis wherein the inhibition of angiogenesis and/or cell proliferation is beneficial.

Hence, in some embodiments the bone related disease or disorder is associated with angiogenesis.

Tumor growth and metastasis are particularly dependent on the degree of angiogenesis. Tumor angiogenesis is the proliferation of a network of blood vessels that penetrate into cancerous tumors in order to supply nutrients and oxygen and remove waste products, thus leading to tumor growth. Tumor angiogenesis involves hormonal stimulation and activation of oncogenes, expression of angiogenic growth factors, extravasation of plasma protein, deposition of a provisional extracellular matrix (ECM), degradation of ECM, and migration, proliferation and elongation of endothelial capillaries. Inhibition of further vascular expansion has therefore been the focus of active research for cancer therapy.

As demonstrated in the Examples section that follows, an exemplary conjugate, according to some embodiments described herein, being a HPMA copolymer of Paclitaxel and alendronate (HPMA copolymer-PTX-FK-ALN conjugate; SEQ ID NO:12) when administered to mice suffering from DA3 murine mammary cancer injected intra-tibia (serving as a model of aggressive tumor cells migrate towards the bones), was able to inhibit the growth of the tumor by 37% whereas administration of Paclitaxel alone had no therapeutic effect (see, FIG. 11).

Hence, in some embodiments the bone related disease or disorder is selected from the group consisting of bone cancer metastases and bone cancer.

The terms "cancer" and "tumor" are used interchangeably herein to describe a class of diseases in which a group of cells display uncontrolled growth (division beyond the normal limits). The term "cancer" encompasses malignant and benign tumors as well as disease conditions evolving from primary or secondary tumors. The term "malignant tumor" describes a tumor which is not self-limited in its growth, is capable of invading into adjacent tissues, and may be capable of spreading to distant tissues (metastasizing). The term "benign tumor" describes a tumor which is not malignant (i.e. does not grow in an unlimited, aggressive manner, does not invade surrounding tissues, and does not metastasize). The term "primary tumor" describes a tumor that is at the original site where it first arose. The term "secondary tumor" describes a tumor that has spread from its original (primary) site of growth to another site, close to or distant from the primary site.

The term "bone cancer" describes tumors that arise from the tissues of the bone. The term "bone cancer", as used herein, further encompasses tumors in tissues located in proximity to bone structures and associated with bone such as cartilage, bone cavity and bone marrow. The term "Bone cancer" further encompasses cancer which evolved from bone cells (i.e. primary tumor) as well as cancer cells which have "breaken away", "leaked", or "spilled" from a primary tumor located in bone, entered the lymphatic and/or blood vessels, circulated through the lymphatic system and/or bloodstream, settled down and proliferated within normal tissues elsewhere in the body thereby creating a secondary tumor. For example, metastases originating from osteosarcoma can be frequently found in the lungs and in other organs. These lesions produce an osteoid and therefore can be targeted similarly with compounds with high affinity to bone mineral, hydroxyapatite, such as alendronate, and other bisphosphonates as well as oligoaspartates.

Bone cancer is found most often in the bones of the arms and legs, but it can occur in any bone.

Bone cancers are also known as sarcomas. There are several types of sarcomas of bone, depending upon the kind of bone tissue where the tumor developed. Exemplary types of bone cancers that are treatable according to embodiments of the invention include, but are not limited to, osteosarcoma, Ewing's sarcoma, chondrosarcoma, fibrosarcoma, malignant giant cell tumor, and chordoma.

Osteosarcoma is the most common type of primary bone cancer and classified as a malignant mesenchymal neoplasm in which the tumor directly produces defective osteoid (immature bone). It is a highly vascular and extremely destructive malignancy that most commonly arises in the metaphyseal ends of long bones. Several strategies were proposed, such as immune-based therapy, tumor-suppressor or suicide gene therapy, or anticancer drugs that are not commonly used in osteosarcoma [Quan et al. *Cancer Metastasis Rev* 2006; 10: 707-713]. However, still one-third of patients die from this devastating cancer, and for those with unresectable disease there are no curative systemic therapies.

The term "bone metastases" describes cancer evolving form a primary tumor located in bodily site other than bone but metastasizing to the bone (i.e. a secondary tumor). Cancers that commonly metastasize, or spread, to the bones include breast cancer, lung cancer, thyroid cancer, prostate cancer, some brain cancers and cancers of the kidney.

For example, prostate cancer is the most common cancer of males in industrialized countries and the second leading cause of male cancer mortality. Prostate cancer predominantly metastasizes to bone, but other organ sites are affected including the lung, liver, and adrenal gland. Bone metastases incidence in patients with advanced metastatic disease is approximately 70%. Bone metastases are associated with considerable skeletal morbidity, including severe bone pain, pathologic fracture, spinal cord or nerve root compressions, and hypercalcemia of malignancy.

As demonstrated in the Examples section that follows, an exemplary conjugate, according to some embodiments described herein, being a HPMA copolymer of Paclitaxel and alendronate (HPMA copolymer-PTX-FK-ALN conjugate; SEQ ID NO: 12) effectively inhibited human prostate PC3 cell line (see, FIG. 10) thereby suggesting the use of the conjugates described herein in the treatment of Prostate cancer metastasizing to bone.

As discussed hereinabove, the conjugates described herein may be further utilized for monitoring bone related disease or disorders. In such a case the conjugate further comprises a labeling agent, as defined herein for easy detection of the conjugate in the body of the patient, using well known imaging techniques. For example, in the case of the bone related disease or disorder being bone cancer the detection of the conjugate, as assessed by the level of labeling agent signal, can serve to detect bone cancer metastases in bodily sites other than bone.

Hence, according to another aspect of some embodiments of the present invention there are provides methods of monitoring a bone related disease or disorder in a subject. The method according to these embodiments of the invention is effected by administering to the subject any of the conjugates described herein, having a labeling agent attached to the polymer, as described herein, and employing an imaging technique for monitoring a distribution of the conjugate within the body or a portion thereof.

Accordingly, according to another aspect of some embodiments of the present invention there are provided uses of any of the conjugates described herein, having a labeling agent as described herein, as diagnostic agents and/or in the manufacture of a diagnostic agent for monitoring a bone related disease or disorder.

According to another aspect of some embodiments of the present invention, each of the conjugates described herein, which comprises a labeling agent, is identified for use as a diagnostic agent, for monitoring a bone related disease or disorder.

Suitable imaging techniques include but are not limited to positron emission tomography (PET), gamma-scintigraphy, magnetic resonance imaging (MRI), functional magnetic resonance imaging (FMRI), magnetoencephalography (MEG), single photon emission computerized tomography (SPECT) computed axial tomography (CAT) scans, ultrasound, fluoroscopy and conventional X-ray imaging. The choice of an appropriate imaging technique depends on the nature of the labeling agent, and is within the skill in the art. For example, if the labeling agent comprises Gd ions, then the appropriate imaging technique is MRI; if the labeling agent comprises radionuclides, an appropriate imaging technique is gamma-scintigraphy; if the labeling agent comprises an ultrasound agent, ultrasound is the appropriate imaging technique, etc.

According to another aspect of the present invention there is provided a pharmaceutical composition comprising, as an active ingredient, any of the conjugates described herein and a pharmaceutically acceptable carrier.

Accordingly, in any of the methods and uses described herein, any of the conjugates described herein can be provided to an individual either per se, or as part of a pharmaceutical composition where it is mixed with a pharmaceutically acceptable carrier.

As used herein a "pharmaceutical composition" refers to a preparation of one or more of the conjugates described herein (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, by inhalation, or parenterally, for example by intravenous drip or intraperitoneal, subcutaneous, intramuscular or intravenous injection, or topically (including ophtalmically, vaginally, rectally, intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an antibacterial agent, an antioxidant, a buffering agent, a bulking agent, a surfactant, an anti-inflammatory agent, an anti-viral agent, a chemotherapeutic agent and an anti-histamine.

According to an embodiment of the present invention, the pharmaceutical composition described hereinabove is packaged in a packaging material and identified in print, in or on the packaging material, for use in the treatment of bone related disease or disorder.

According to another embodiment of the present invention, the pharmaceutical composition is packaged in a packaging material and identified in print, in or on the packaging material, for use in monitoring a bone related disease or disorder.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

In any of the methods, uses and compositions described herein, the conjugates described herein can be utilized in combination with additional therapeutically active agents. Such additional agents include, as non-limiting examples, chemotherapeutic agents, anti-angiogensis agents, hormones, growth factors, antibiotics, anti-microbial agents, anti-depressants, immunostimulants, and any other agent that may enhance the therapeutic effect of the conjugate and/or the well-being of the treated subject.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Materials and Methods

Materials:

All reactions requiring anhydrous conditions were performed under an argon and nitrogen atmosphere.

HPMA copolymer-Gly-Gly-p-nitrophenol (ONp) (SEQ ID NO: 22) incorporating 5 mol % of the methacryloyl-Gly-Gly-p-nitrophenol ester monomer units (SEQ ID NO: 23), and HPMA copolymer-Gly-Phe-Leu-Gly-ONp (SEQ ID NO: 21) incorporating 10 mol % of the methacryloyl-Gly-Phe-Leu-Gly-p-nitrophenol ester monomer units (SEQ ID NO: 24) were obtained from Polymer Laboratories (Church Stretton, UK). The HPMA copolymer-GFLG-ONp (SEQ ID NO: 21) has a molecular weight of 31,600 Da and a polydispersity of 1.66.

PTX and ALN were purchased from Petrus Chemicals and Materials Ltd.

Bovine spleen cathepsin B, hydroxyapatite (HA), cathepsin B inhibitor (CA-074 methyl ester) and all chemical reagents, including salts and solvents, were purchased from Sigma-Aldrich.

Chemicals and solvents were either A.R. grade or purified by standard techniques.

Thin layer chromatography (TLC): silica gel plates Merck 60 $F_{254}$; compounds were visualized by irradiation with UV light and/or by treatment with a solution of phosphomolybdic acid (20% wt. in ethanol), followed by heating.

Flash chromatography (FC): silica gel Merck 60 (particle size 0.040-0.063 mm), eluent given in parentheses.

$^1$H NMR: Bruker AMX 200 or 400 instrument. The chemical shifts are expressed in δ relative to TMS (δ=0 ppm) and the coupling constants J in Hz. The spectra were recorded in $CDCl_3$, as a solvent at room temp.

400 Mesh copper grid was purchased from SPI Supplies, West Chester, Pa.

Cell Culture:

Human umbilical endothelial cells (HUVEC) were purchased from Lonza, Switzerland. Cells were cultured in EGM-2 medium (Lonza, Switzerland) and were grown at 37° C.; 5% $CO_2$. The human prostate cell line PC3 was purchased from the American Type Culture Collection. PC3 cells were cultured in DMEM supplemented with 10% FBS, 100 μg/ml Penicillin, 100 U/ml Streptomycin, 12.5 U/ml Nystatin and 2 mM L-glutamin. Cells were grown at 37° C.; 5% $CO_2$.

Characterization of HPMA Copolymer-Paclitaxel-FK-ALN Conjugate:

Determination of ALN Content:

HPMA copolymer-paclitaxel-FK-ALN conjugate (SEQ ID NO: 12) (3.4, 1.7 and 0.85 mg) was dissolved in a mixture of 0.8 ml of 0.2M perchloric acid ($HClO_4$) and 0.1 ml of 4 mM $FeCl_3$. The content of ALN in HPMA copolymer-paclitaxel-FK-ALN conjugate (SEQ ID NO: 12) was determined against a calibration graph of serial dilutions of 0-3 mM ALN. Samples absorbance was measured spectrophotometrically at λ=300 nm.

Quantitative Evaluation of HPMA Copolymer-Paclitaxel-FK-ALN Conjugate Hydrodynamic Diameter and Size Distribution:

The mean hydrodynamic diameter of the conjugate was evaluated using a real time particle analyzer (NanoSight LM20™) containing a solid-state, single mode laser diode (<20 mW, 655 nm) configured to launch a finely focused beam through a 500 μL sample chamber. HPMA copolymer-paclitaxel-FK-ALN conjugate (SEQ ID NO: 12) was dissolved in PBS to final concentrations of 2, 1, 0.5 mg/ml. The samples were then injected into the chamber by syringe and allowed to equilibrate to unit temperature (230° C.) for 30 seconds. The particles dynamics were visualized at 30 frames per second (fps) for 60 seconds at 640×480 resolution by the device CCD camera. The paths the particles take under Brownian motion over time were analyzed using Nanoparticle Tracking Analysis (NTA) software. The diffusion coefficient and hence sphere equivalent hydrodynamic radius of each particle was separately determined and the particle size distribution profiles were generated. Each sample was measured three times in triplicates, and the results represent the mean diameter.

Cell Proliferation Assay:

Human Umbilical vain endothelial cells (HUVEC) were plated onto 24-well plate (1×10$^4$ cells/well) in growth factors reduced media, (EBM-2, Cambrex, USA) supplemented with 5% Fetal Bovine Serum (FBS). Following 24 hours of incubation (37° C.; 5% $CO_2$) medium was replaced with EGM-2 (Cambrex, USA). PC3 cells were plated onto 96 well plate (2×103 cells/well) in DMEM supplemented with 5% FBS and incubated for 24 hours (37° C.; 5% CO2). Following 24 hours of incubation medium was replaced with DMEM containing 10% FBS. Cells were challenged with a combination of paclitaxel and ALN, a combination of Paclitaxel-FK and ALN, with each drug alone, and with HPMA copolymer-paclitaxel-FK-ALN conjugate (SEQ ID NO: 12), at serial concentrations for 72 hours. Control cells were grown with or without growth factors. After incubation HUVEC and PC3 were counted by Coulter Counter or by XTT respectively.

Capillary-Like Tube Formation Assay:

The surface of 24-well plates was coated with Matrigel matrix (50 μl/well; BD Biosecience, USA) on ice and was then allowed to polymerize at 37° C. for 30 minutes. HUVEC (3×10$^4$) were challenged with a combination of Paclitaxel and ALN, a combination of Paclitaxel-FK (SEQ ID NO: 13) and ALN, with each drug alone, and with HPMA copolymer-Paclitaxel-FK-ALN conjugate (SEQ ID NO: 12), and were seeded on coated plates in the presence of complete EGM-2 medium. After 8 hours of incubation (37° C.; 5% $CO_2$), wells were imaged using Nikon TE2000E inverted microscope integrated with Nikon DS5 cooled CCD camera by 4× objective, brightfield technique.

Human Umbilical Vain Endothelial Cells (HUVEC) Migration Assay:

Cell migration assays were performed using modified 8 μm Boyden chambers Transwells® (Costar Inc., USA) coated with 10 μgram/ml fibronectin (Biological industries, Beit Haemek, Israel). HUVEC (15×10$^4$ cells/100 μl) were challenged with a combination of Paclitaxel and ALN, a combination of Paclitaxel-FK (SEQ ID NO: 13) and ALN, with each drug alone, and with HPMA copolymer-Paclitaxel-FK-ALN conjugate (SEQ ID NO: 12) and were added to the upper chamber of the transwell for 2 hours incubation prior to migration to vascular endothelial growth factor (VEGF). Following incubation, cells were allowed to migrate to the underside of the chamber for 4 hours in the presence or absence of VEGF (20 ng/ml) in the lower chamber. Cells were then fixed and stained using Hema 3 Stain System (Fisher Diagnostic, USA). The stained migrated cells were imaged using Nikon TE2000E inverted microscope integrated with Nikon DS5 cooled CCD camera by 10× objective, brightfield illumination. Migrated cells from the captured images per membrane were counted using NIH image software. Migration was normalized to percent migration, with 100% representing VEGF dependent migration of cells which were not incubated with any drug.

Enzymatic Release of Paclitaxel from HPMA-Paclitaxel-FK-ALN (SEQ ID NO: 12) by Cathepsin B and Paclitaxel Content Determination:

Paclitaxel and ALN were released from HPMA copolymer-paclitaxel-FK-ALN (SEQ ID NO: 12) by bovine spleen cathepsin B at conditions mimicking lysosomal intracellular drug release. HPMA copolymer-paclitaxel-FK-ALN (SEQ ID NO: 12) (7 mg/ml, 0.5 mM Paclitaxel-equivalent) were incubated at 37° C. in phosphate buffer (0.1 M sodium phosphate, 0.05 M NaCl, 1 mM EDTA, pH 6), reduced glutathione (5 mM), and cathepsin B (0.5 μM). Aliquots of 300 μl were taken after 12, 24 and 48 hours. Free Paclitaxel was extracted at 0.2 M $Na_2CO_3$/$NaHCO_3$, pH 9.8 by 100% EtOAc. Free Paclitaxel concentration was analyzed by high pressure liquid chromatography (HPLC, AKTA™ Purifier®, Amersham Biosciences, μBondapak™ C18 3.9×150 mm column, Waters, acetonitrile-water gradient of 30-100% acetonitrile, at 1 ml/min, λ=245 nm) against calibration curve of paclitaxel which was not incubated with cathepsin B, and extracted at the same conditions, for calibration.

Hydroxyapatite Binding Assay:

HPMA copolymer-Paclitaxel-FK-ALN conjugate (SEQ ID NO: 12) was dissolved in phosphate buffered saline (PBSX1), pH 7.4 (1 mg/ml). The conjugate solution (500 μl) was incubated with hydroxyapatite powder (15 mg), in 500 μl PBS, pH 7.4. HPMA copolymer-Gly-Phe-Leu-Gly (SEQ ID NO: 25) was used as control. Incubated samples were centrifuged at 6000 RPM for 3 minutes and a sample from the upper layer (100 μl) was collected at selected time points. Fast Protein Liquid Chromatography (FPLC, AKTA™ Purifier®, Amersham Biosceinces) analysis using HighTrap™ desalting column (Amersham®) was used for detection of unbound conjugate in the samples (FPLC conditions: AKTA™ Purifier®, mobile phase 100% DDW, 2 ml/min, λ=215 nm). Hydroxyapatite-binding kinetic analysis of the conjugate was performed using the Unicorn AKTA™ software. Areas under the curve (AUC) were calculated from chromatographs at each time point. AUC of each Hydroxyapatite-incubated conjugate chromatogram was normalized to percent AUC of conjugate sample in the absence of Hydroxyapatite.

Evaluation of Antitumor Activity of HPMA Copolymer-PTX-FK-ALN Conjugate In Vivo:

9 Balb/c female mice (n=3 per group) were injected intra tibia with $5 \times 10^5$ mCherry-labeled DA3 murine mammary cancer cells. Mice bearing tumors were injected i.p. with a combination of free ALN and PTX (1:1.6, 1.25 mg/kg ALN and 2 mg/kg PTX), equivalent dose of HPMA copolymer-PTX-FK-ALN conjugate (SEQ ID NO: 12) or with vehicle (1:1:8 cremophor EL:ethanol:saline). Therapy was initiated 10 days after tumor cells injection. Tumor progression was monitored by CRI™ Maestro non-invasive intravital imaging system. At termination, tibias were weighed and analyzed. Data is expressed as mean±standard error of the mean (s.e.m.).

Statistical Methods:

Data are expressed as mean±SD. Statistical significance was determined using an unpaired t-test. $p < 0.05$ was considered statistically significant. All statistical tests were two-sided.

Example 1

Synthesis of HPMA Copolymer-Paclitaxel-FK-ALN Conjugate (SEQ ID NO: 12)

An exemplary general synthesis of an HPMA copolymer-Paclitaxel-FK-ALN (SEQ ID NO: 12) (Compound 1) is depicted in FIG. 2A.

Preparation of Compound 2:

L-Boc-Phe-ONp (104.3 mg, 0.27 mM) was dissolved in 2 ml Dimethylformamide (DMF). Then, commercially available L-Lys(alloc)-OH (62 mgram, 0.27 mM) and $Et_3N$ (100 μL) were added. The reaction mixture was stirred for 12 hours while being monitored by TLC (AcOH:MeOH:EtOAc 0.5:10:89.5). Upon completion of the reaction, the solvent was removed under reduced pressure and the crude product was purified by column chromatography on silica gel (AcOH:MeOH:EtOAc 0.5:10:89.5) to give Compound 2 (107 mg, 83%) as a white solid.

$^1$H NMR (200 MHz, $CDCl_3$): δ=7.24-7.11 (5H, m); 5.83 (1H, m); 5.45-5.11 (3H, m); 4.50-4.48 (3H, m); 3.08-2.92 (4H, m); 1.84-1.64 (2H, m); 1.44-1.36 (4H, m); 1.30 (9H, s) ppm.

$^{13}$C NMR (100 MHz, $CDCl_3$): δ=177.09, 164.91, 158.52, 157.61, 138.45, 134.82, 131.26, 130.50, 128.83, 120.24, 82.27, 67.51, 57.59, 53.98, 42.37, 38.60, 33.53, 33.44, 30.14, 22.63 ppm.

MS (FAB): m/z: 478.3 $[M+H]^+$, 500.3 $[M+Na]^+$.

Preparation of Compound 3:

Compound 2 (832.1 mg, 1.74 mM) was dissolved in dry tetrahydrofurane (THF) and the solution was cooled to −15° C. followed by the addition of NMM (0.19 ml, 1.74 mM) and isobutyl chloroformate (0.27 ml, 2.09 mM). The reaction was stirred for 20 minutes and a solution of 4-aminobenzyl alcohol (321.85 mg, 2.61 mM) in dry THF was added. The reaction mixture was stirred for 2 hours and was monitored by TLC (EtOAc 100%). Upon completion of the reaction, the solvent was removed under reduced pressure and the crude product was purified by column chromatography on silica gel (EtOAc 100%) to give Compound 3 (835 mg, 82%) as a yellow solid.

$^1$H NMR (200 MHz, MeOD): δ=7.56 (2H, d, J=8 Hz); 7.29 (2H, d, J=8 Hz); 7.21-7.07 (5H, m); 5.86 (1H, m); 5.29-5.10 (2H, m); 4.83 (2H, s); 4.49-4.46 (4H, m); 3.17-3.08 (4H, m); 1.88-1.70 (2H, m); 1.44 (4H, m); 1.34 (9H, s) ppm.

$^{13}$C NMR (100 MHz, $CDCl_3$): δ=174.08, 171.45, 158.61, 157.79, 139.17, 138.87, 138.03, 134.79, 131.12, 130.71, 130.49, 129.90, 129.08, 122.15, 82.71, 67.48, 66.83, 58.08, 55.74, 42.09, 39.84, 32.70, 31.31, 30.16, 24.31 ppm.

MS (FAB): m/z: 583.3 $[M+H]^+$, 605.3 $[M+Na]^+$.

Preparation of Compound 4:

Compound 3 (353.6 mg, 0.60 mM) was dissolved in dry THF and the solution was cooled to 0° C. Then diisopropylethylamine (DIPEA; 0.42 ml, 2.42 mM), PNP-chloroformate (367 mg, 1.82 mM) and a catalytic amount of pyridine were added. The reaction mixture was stirred for 2 hours and was monitored by TLC (EtOAc:Hex 3:1). Upon completion of the reaction, the solvent was removed under reduced pressure. The crude product was diluted with EtOAc and washed with saturated $NH_4Cl$. The organic layer was dried over magnesium sulfate and the solvent was removed under reduced pressure. The crude product was purified by column chromatography on silica gel (EtOAc:Hex 3:1) to give Compound 4 (453.2 mgram, 79%) as a white solid.

$^1$H NMR (200 MHz, $CDCl_3$): δ=8.26 (2H, d, J=8 Hz); 7.64 (2H, d, J=8 Hz); 7.40-7.34 (4H, m); 7.22-7.14 (5H, m); 5.83 (1H, m); 5.24 (2H, s); 5.18-5.06 (2H, m); 4.56-4.37 (4H, m); 3.19-3.05 (4H, m); 1.95-1.73 (2H, m); 1.59-1.46 (4H, m); 1.39 (9H, s) ppm.

$^{13}$C NMR (100 MHz, $CDCl_3$): δ=174.11, 171.51, 158.63, 157.60, 157.46, 154.36, 147.32, 140.70, 137.91, 134.76, 131.75, 131.53, 131.08, 130.78, 129.17, 127.21, 123.72, 122.05, 119.61, 82.86, 72.65, 67.50, 58.17, 55.84, 41.95, 39.71, 32.42, 31.40, 30.16, 24.27 ppm.

MS (FAB): m/z: 770.4 $[M+Na]^+$.

Preparation of Compound 5:

Compound 4 (360.3 mg, 0.48 mM) was dissolved in dry dichloromethane (DCM). Then paclitaxel (494.06 mg, 0.57 mM) and dimethylaminopyridine (DMAP) (70.61 mg, 0.57 mM) were added. The reaction mixture was stirred for 8 hours and was monitored by TLC (EtOAc 100%). Upon completion of the reaction, the solvent was removed under reduced pressure and the crude product was purified by using column chromatography on silica gel (EtOAc 100%) to give Compound 5 (662 mg, 94%) as a white solid.

MS (FAB): m/z: 1463.7 [M], 1486.9 $[M+Na]^+$.

Preparation of Compound 6:

Compound 5 (82.1 mg, 56.1 μM) was dissolved in 1.5 ml trifluoroacetic acid (TFA) and the solution was stirred for 2 minutes at 0° C. The excess of acid was removed under reduced pressure and the crude amine salt was dissolved in 2 ml DMF. HPMA copolymer-Gly-Phe-Leu-Gly-ONp (SEQ ID NO: 21; 198 mg, ONp=66.0 μmol) was added followed by the addition of Et$_3$N (100 μl). The reaction mixture was stirred for 12 hours and the solvent was removed under reduced pressure. The crude product was used for the next step without further purification.

Preparation of Compound 7:

ALN (100 mg, 30.8 μM) was dissolved in water (1 ml). While stirring the sample, a solution of crude Compound 6 (80 mg, ONp=max. 26.6 μmol) in DMF (350 μl) was added dropwise into the aqueous solution and NaOH (0.2 M) was then dropped into the solution. Slowly, the pH value was increased to 7. Then, in 1 hour, the pH was further increased to 8. The pH value of the reaction mixture was thereafter quickly raised to 9, to finalize the reaction. Free amine Compound 6, ONp and ALN were removed with FPLC using XK26/70 column with Sephadex LH20 column chromatography (MeOH 100%, 1 ml/1 minute) to give Compound 7 as a white solid (47 mg).

Preparation of Compound 1:

Compound 7 (47 mg, alloc=max. 15.6 μM) was dissolved in DMF (1.5 ml). Then acetic acid (4.46 μl, 78 μM), Bu$_3$SnH (25.17 μl, 93.6 mM) and a catalytic amount of Pd (PPh$_3$)$_4$ were added. The reaction mixture was stirred for 2 hours and was thereafter concentrated under reduced pressure, followed by addition of 10 ml of acetone. The precipitate was filtered out and was washed with acetone several times. The crude product was purified by HPLC using XK26/70 column with Sephadex LH20 (MeOH 100%, 1 ml/1 minute) to give compound 1 (32 mg) as a white solid.

Quantitative Evaluation of HPMA Copolymer-Paclitaxel-FK-ALN Conjugate (SEQ ID NO: 12) Size Distribution:

The hydrodynamic diameter and size distribution of the polydispersed nanoscale HPMA copolymer-PTX-FK-ALN conjugate (SEQ ID NO: 12) were then characterized by laser light scattering microscopy with nanoparticle tracking analysis (NTA) technology (NanoSight LM20, Salisbury, UK). The mean hydrodynamic diameter of the conjugate was 95 nm (FIG. 2B).

In an alternative synthetic route, the HPMA copolymer-PTX-ALN (SEQ ID NO: 12) conjugate was prepared using the RAFT methodology, as detailed hereinabove, and is depicted in FIG. 2C. Conjugates prepared by the RAFT approach are typically characterized by low PDI (e.g., lower than 1.4).

Example 2

Binding of HPMA Copolymer-Paclitaxel-FK-ALN Conjugate (SEQ ID NO: 12) to Hydroxyapatite The bisphosphonate ALN, known as bone targeting moiety with strong bone affinity, was chosen as the bone targeting moiety. The binding capacity of the conjugate to bone mineral was evaluated. Hydroxyapatite was used as a model mimicking bone tissue. An in vitro hydroxyapatite binding assay and FPLC analysis using Hitrap desalting column was performed (FIG. 3A). Unbound conjugates eluted as a single peak with a retention time of 2 minutes. The Area Under the Curve (AUC), corresponding to the amount of unbound conjugate eluted, decreased in correlation with hydroxyapatite incubation time. HPMA copolymer-paclitaxel-FK-ALN (SEQ ID NO: 12) was rapidly adsorbed to hydroxyapatite. Following 5 minutes of incubation, 43% of the conjugate in the solution was bound to hydroxyapatite (FIG. 3B). This rapid binding rate to hydroxyapatite reached a plateau after 30 minutes of incubation time with about 50% of bound conjugate.

Example 3

Determination of Alendronate Loading in the HPMA Copolymer-Paclitaxel-FK-ALN Conjugate (SEQ ID NO: 12)

The loading of ALN onto the HPMA copolymer-paclitaxel-FK-ALN conjugate (SEQ ID NO: 12) was determined spectrophotometrically via chromophoric complex formation between ALN and Fe$^{3+}$ ions in perchloric acid, and against a calibration graph of ALN. 2.5 mol % out of the 10 mol % of the Gly-Phe-Leu-Gly-ONp chains (SEQ ID NO: 26) of the HPMA copolymer were found to be bound to ALN. This percentage surpasses the amount needed for bone targeting, as indicated previously [see, Wang et al. 2003, *Bioconjugate Chem* 14:853].

Example 4

Enzymatic Release of Paclitaxel from HPMA-Paclitaxel-FK-ALN (SEQ ID NO:12) by Cathepsin B and Paclitaxel Loading Determination Cathepsin B which is overexpressed in tumor and endothelial cells was used in vitro to cleave the HPMA copolymer-paclitaxel-FK-ALN conjugate (SEQ ID NO: 12) at (1) the two amide bonds of the paxlitaxel-hexapeptide linker (between Gly-Phe-Leu-Gly (SEQ ID NO: 3) and the Phe-Lys (SEQ ID NO:10) amino acids, and between the Phe-Lys (SEQ ID NO: 10) and the p-aminobenzyl carbonate (PABC)) and (2) the amide bond of the ALN tetrapeptide linker (the Gly-Phe-Leu-Gly; SEQ ID NO:3) at 37° C., pH 5.5. The products of the cathepsin B cleavage were PABC-Paclitaxel and ALN. Free Paclitaxel, the final product, was obtained from PABC-Paclitaxel through spontaneous 1,6-benzyl elimination (schematic illustration presented in FIG. 1). Samples were taken after 12, 24, 48 hours and 72 hours, and the content of Paclitaxel in HPMA copolymer-Paclitaxel-FK-ALN conjugate (SEQ ID NO:12) was determined using HPLC analysis. Free Paclitaxel was eluted as a single peak with a retention time of 10.55 minutes. AUC increased in correlation with cathepsin B incubation time (FIGS. 4A and 4B).

Paclitaxel loading onto the polymer was also determined against free Paclitaxel calibration curve. 4 mol % out of the 10 mol % of the Gly-Phe-Leu-Gly-ONp chains (SEQ ID NO: 26) present in the HPMA copolymer, were found to be bound to Paclitaxel.

Example 5

Effect of HPMA Copolymer-Paclitaxel-FK-ALN (SEQ ID NO: 12) on the Proliferation of HUVEC As an attempt to evaluate whether paclitaxel and ALN, when bound to HPMA copolymer, retained their anti-angiogenic effect, a proliferation, migration and capillary like tube formation were performed.

The proliferation of HUVEC was inhibited similarly by the combination of paclitaxel-FK (SEQ ID NO: 13)+ALN and HPMA copolymer-Paclitaxel-FK-ALN conjugate (SEQ ID NO: 12) at Paclitaxel/FK/ALN equivalent concentrations, exhibiting an $IC_{50}$ of about 10 nM and about 2.5 nM respectively (FIG. 5). ALN, which is known to exhibit an anti-angiogenic effect at concentrations of 1-100 µM had no additional effect on the proliferation of HUVEC when combined with Paclitaxel, or with Paclitaxel-FK (SEQ ID NO: 13) at the tested concentrations (10 µM-0.001 nM). ALN alone inhibited the proliferation of HUVEC only at the highest dose tested of 6.25 µM. HPMA alone was inert in vitro and in vivo in agreement with previously published data.

Example 6

Non-Cleavable HPMA Copolymer-GGGG-PTX (SEQ ID NO:14) Vs. The Cathepsin B-Cleavable HPMA Copolymer-GGFK-PTX Conjugate (SEQ ID NO: 15)

To prove that the HPMA copolymer-PTX-FK-ALN conjugate (SEQ ID NO: 12) is active mainly upon the release of PTX by cleavage with cathepsin B, and not by spontaneous hydrolysis, an HPMA copolymer-GGGG-PTX conjugate (SEQ ID NO: 14) containing the non-cleavable Gly-Gly (GG) linker (SEQ ID NO:27) was synthesized (2D chemical structure shown in FIG. 6A) and compared with the cleavable HPMA copolymer-GGFK-PTX conjugate (SEQ ID NO: 15; 2D chemical structure shown in FIG. 6B). The HPMA copolymer-GGGG-PTX conjugate (SEQ ID NO: 14) inhibited the proliferation of human umbilical-vein endothelial cells (HUVECs) with an $IC_{50}$ value of approximately 10,000 nM, that is, at a concentration two orders of magnitude higher than that required for the HPMA copolymer-GGFK-PTX conjugate (SEQ ID NO: 15) ($IC_{50}$ 100 nM), which is cleaved by cathepsin B (see, FIG. 6C). Following 72 hours, some paclitaxel hydrolytic release was observed, which lead to inhibition of proliferation at concentrations higher than 100 nM Paclitaxel-equivalent.

These findings further supports the notion that PTX-FK (SEQ ID NO: 13) bound to the HPMA copolymer is released mainly through cleavage by cathepsin B.

Example 7

Cathepsin B Inhibitor Reduces PTX-FK (SEQ ID NO: 13) and HPMA Copolymer-PTX-FK-ALN Conjugate (SEQ ID NO: 12) Cytotoxicity In order to further prove that HPMA copolymer-PTX-ALN conjugate (SEQ ID NO: 12) is active mainly upon the release of PTX by cathepsin B cleavage, and not by spontaneous hydrolysis, a proliferation assay on HUVECs in the presence and absence of cathepsin B inhibitor was performed. As shown in FIG. 7, HUVECs were incubated with HPMA copolymer-PTX-FK-ALN conjugate (SEQ ID NO: 12) and with a combination of free PTX-FK (SEQ ID NO; 13)+free ALN at equivalent concentrations of 500 nM and 300 nM respectively. Following 48 hours HPMA copolymer-PTX-FK-ALN conjugate (SEQ ID NO: 12) inhibited the proliferation of HUVEC by about 27% and about 40% in the presence or absence of cathepsin B inhibitor, respectively. Similarly, the proliferation of HUVECs was diminished by about 25% and about 50% by PTX-FK (SEQ ID NO:13)+ALN with or without cathepsin B inhibitor correspondingly.

Example 8

Effect of HPMA Copolymer-Paclitaxel-FK-ALN Conjugate (SEQ ID NO: 12) on Migration of HUVEC Toward VEGF In Vitro The effect of the HPMA copolymer-PTX-FK-ALN conjugate (SEQ ID NO: 12) on the ability of HUVECs to migrate towards vascular endothelial growth factor (VEGF) was tested. The HPMA copolymer-PTX-FK-ALN conjugate (SEQ ID NO:12) and a combination of free PTX-FK (SEQ ID NO: 13)+free ALN at equivalent concentrations of 100 and 60 nM, respectively, inhibited the migration of HUVECs towards VEGF by approximately 35%, as shown in FIG. 8.

Example 9

Effect of HPMA Copolymer-Paclitaxel-FK-ALN Conjugate (SEQ ID NO: 12) on Capillary-Like Tube Formation of HUVEC In Vitro Having shown that free and conjugated paclitaxel-FK-ALN (SEQ ID NO: 12) have anti-angiogenic potential by inhibiting the proliferation and migration of HUVECs, the effect of these drugs on the ability of HUVECs to form capillary-like tube structures on matrigel was tested (see, FIG. 9A). HPMA copolymer-paclitaxel-FK-ALN (SEQ ID NO: 12) and the combination of free Paclitaxel-FK (SEQ ID NO:13)+free ALN at equivalent concentrations of 0.5 and 0.3 nM, respectively, inhibited the formation of tubular structure of HUVEC by about 65% (FIG. 9B). HPMA served as control and had no inhibitory effect on the ability of HUVEC to form tubular structure.

Example 10

Effect of HPMA Copolymer-Paclitaxel-FK-ALN (SEQ ID NO:12) on the Proliferation of Human Prostate Cell Line PC3

There have been several reports indicating PTX as an effective agent that could be used to treat advanced metastatic prostate cancer. The retention of the cytotoxic activity of PTX and ALN, when bound to HPMA copolymer, on the proliferation of the human prostate PC3 cell line was evaluated. The proliferation of PC3 cells was inhibited by HPMA copolymer-PTX-FK-ALN conjugate (SEQ ID NO:12) and the combination of free PTX-FK (SEQ ID NO:13)+free ALN at equivalent concentrations, exhibiting an $IC_{50}$ of about 10 mM PTX-FK (SEQ ID NO:13) and about 6 µM ALN (FIG. 10). PTX alone exhibited an $IC_{50}$ of 1 µM. ALN, alone or when combined with PTX, or with PTX-FK at the concentrations tested of 0.01 nM-10 µM had no effect on the proliferation of PC3 cells.

Example 11

HPMA Copolymer-Paclitaxel-FK-ALN Conjugate (SEQ ID NO:12) Inhibits DA3 Mammary Tumors in the Tibia In Vivo Balb/c female mice bearing mCherry-labeled DA3 tumors in the tibia were treated with free and conjugated ALN and PTX (1:1.6, 1.25 mg/kg ALN and 2 mg/kg PTX, every day). Tumor growth rates were measured and monitored by mCherry fluorescence signal using CRI™ Maestro non-invasive intravital imaging system. Both treatments of the combination of free PTX and ALN and HPMA copolymer-PTX-FK-ALN conjugate (SEQ ID NO: 12) exhibited antitumor activity (see, FIG. 11A). Following 9 days of treatment, a 37% inhibition in tumor growth of mice treated with HPMA copolymer-PTX-FK-ALN conjugate (SEQ ID NO: 12) and no significant inhibition in mice treated with free ALN and PTX was observed (see, FIG. 11A). HPMA copolymer-PTX-FK-ALN conjugate (SEQ ID NO: 12) did not cause weight loss (see, FIG. 11B). Since weight loss is associated with drug toxicity these results suggest a reduced level of toxicity of the conjugate.

The DA3 murine mammary cancer injected intra-tibia is a very aggressive tumor model imitating a clinical scenario where aggressive tumor cells migrate towards the bones, such as the tibia, and form rapidly-growing metastases. Free PTX had no antitumor effect on this tumor model. Therefore, an inhibition of 37% in tumor growth for the treatment with HPMA copolymer-PTX-FK-ALN conjugate (SEQ ID NO:12) is an unprecedented result. In vivo study on a standard less aggressive tumor model in mice is currently being performed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A conjugate comprising a polymeric backbone having attached thereto an anti-angiogenesis agent and a bisphosphonate bone targeting moiety, said polymeric backbone being derived from a polymer selected from the group consisting of dextran, a water soluble polyamino acid, a polyethylenglycol (PEG), a polyglutamic acid (PGA), a polylactic acid (PLA), a polylactic-co-glycolic (PLGA), a poly(D,L-lactide-co-glycolide) (PLA/PLGA), a polyglycerol, a polyamidoamine (PAMAM), and a polyethylenimine (PEI), the conjugate being represented by the general formula I:

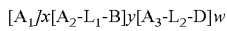   Formula I wherein:

x is an integer having a value such that x/(x+y+w) multiplied by 100 is in the range of from 70 to 99.8;

y is an integer having a value such that y/(x+y+w) multiplied by 100 is in the range of from 0.1 to 15; and w is an integer having a value such that w/(x+y+w) multiplied by 100 is in the range of from 0.1 to 15, $A_1$, $A_2$, and $A_3$ are each backbone units covalently linked to one another and forming said polymeric backbone, wherein:

B is said anti-angiogenesis agent;

D is said bone targeting moiety; and each of the $L_1$ and $L_2$ is independently a linker or absent;

such that [$A_2$-$L_1$-B] is a backbone unit having attached thereto said anti-angiogenesis agent; and

[$A_2$-$L_2$-D] is a backbone unit having attached thereto said bone targeting moiety;

wherein each of the [$A_1$], the [$A_2$-$L_1$-B] and the [$A_3$-$L_2$-D] is either a terminal backbone unit being linked to one of the [$A_1$], the [$A_2$-$L_1$-B] and the [$A_3$-$L_2$-D], or is linked to at least two of the [$A_1$], [$A_2$-$L_1$-B] and the [$A_3$-$L_2$-D], whereby $A_1$, $A_2$ and/or $A_3$ are linked to one another to thereby form said polymeric backbone.

2. The conjugate of claim 1, wherein said anti-angiogenesis agent is paclitaxel.

3. The conjugate of claim 1, wherein said bisphosphonate is alendronate.

4. The conjugate of claim 1, wherein at least one of $L_1$ and $L_2$ is said linker.

5. The conjugate of claim 4, wherein said linker is an enzymatically-cleavable linker.

6. The conjugate of claim 5, wherein said enzymatically-cleavable linker is cleaved by an enzyme which is overexpressed in tumor tissues.

7. The conjugate of claim 6, wherein said enzyme is selected from a group consisting of Cathepsin B, Cathepsin K, Cathepsin D, Cathepsin H, Cathepsin L, legumain, MMP-2 and MMP-9.

8. The conjugate of claim 1, wherein said anti-angiogenesis agent is attached to $L_1$ or to $A_2$ via a spacer.

9. The conjugate of claim 4, wherein said bisphosphonate is attached to $L_2$ and $A_3$ via a spacer.

10. The conjugate of claim 8, wherein said anti-angiogenesis agent is paclitaxel and said paclitaxel is linked to said $L_1$ or said $A_2$ via said spacer.

11. The conjugate of claim 10, wherein said spacer is p-aminobenzyl carbonate (PABC).

12. The conjugate of claim 1, further comprising a labeling agent attached thereto.

13. A pharmaceutical composition comprising, as an active ingredient, the conjugate of claim 1 and a pharmaceutically acceptable carrier.

14. The pharmaceutical composition of claim 13, being packaged in a packaging material and identified in print, in or on said packaging material, for use in the treatment of a bone related disease or disorder.

15. The pharmaceutical composition of claim 13, wherein said conjugate comprises a labeling agent, the composition being packaged in a packaging material and identified in print, in or on said packaging material, for use in monitoring a bone related disease or disorder.

16. A method of treating a bone related disease or disorder in a subject in need thereof, the method comprising administering to the subject a therapeutically effective amount of the conjugate of claim 1.

17. A method of monitoring a bone related disease or disorder in a subject, the method comprising:

administrating to the subject the conjugate of claim 12; and employing an imaging technique for monitoring a distribution of the conjugate within the body or a portion thereof.

18. The method of claim 16, wherein said disease or disorder is selected from the group consisting of bone metastases and bone cancer.

19. The method of claim 17, wherein said disease or disorder is selected from the group consisting of bone metastases and bone cancer.

* * * * *